(12) United States Patent
Itarashiki et al.

(10) Patent No.: US 10,058,106 B2
(45) Date of Patent: Aug. 28, 2018

(54) STERILIZATION METHOD AND STERILIZER

(71) Applicant: SARAYA CO., LTD., Osaka-shi, Osaka (JP)

(72) Inventors: Tomomasa Itarashiki, Osaka (JP); Norio Onitsuka, Osaka (JP)

(73) Assignee: SARAYA CO., LTD., Osaka-Shi, Osaka (JP)

( * ) Notice: Subject to any disclaimer, the term of this patent is extended or adjusted under 35 U.S.C. 154(b) by 294 days.

(21) Appl. No.: 14/431,127

(22) PCT Filed: Sep. 20, 2013

(86) PCT No.: PCT/JP2013/075498
§ 371 (c)(1),
(2) Date: Jul. 13, 2015

(87) PCT Pub. No.: WO2014/050744
PCT Pub. Date: Apr. 3, 2014

(65) Prior Publication Data
US 2015/0313250 A1 Nov. 5, 2015

(30) Foreign Application Priority Data

Sep. 27, 2012 (JP) ................................. 2012-215307

(51) Int. Cl.
*A61L 2/16* (2006.01)
*A61L 2/24* (2006.01)
(Continued)

(52) U.S. Cl.
CPC ............... *A23B 5/022* (2013.01); *A23B 7/02* (2013.01); *A23B 9/08* (2013.01); *A23L 3/015* (2013.01);
(Continued)

(58) Field of Classification Search
CPC ....................................................... A23B 5/022
(Continued)

(56) References Cited

U.S. PATENT DOCUMENTS 5,317,896 A 6/1994 Sheth et al.
5,482,683 A 1/1996 Sheth et al.
(Continued)

FOREIGN PATENT DOCUMENTS

CN 1077532 10/1993
EP 1040839 10/2000
(Continued)

OTHER PUBLICATIONS

International Search Report (PCT/ISA/210) dated Dec. 24, 2013, by the Japanese Patent Office as the International Searching Authority for International Application No. PCT/JP2013/075498.
(Continued)

*Primary Examiner* — Kevin Joyner
*Assistant Examiner* — Holly M Mull
(74) *Attorney, Agent, or Firm* — Buchanan Ingersoll & Rooney PC

(57) ABSTRACT

According to the present invention, a sterilant can be injected into a container without residual water on an object to be sterilized. The method includes decreasing a pressure in the container to a pressure higher than the triple point pressure at which water freezes. The method further includes comparing an actual time required for decreasing the pressure and a reference time, or comparing an actual rate of pressure increase and a reference rate to detect residual water on the object. If the residual water is detected, the pressure in the container is increased to the atmospheric pressure or the quasi-atmospheric pressure and the object is heated, and then the pressure is decreased to drain the residual water through the decompression boiling. The step (Continued)

of draining the residual water is repeatedly performed until no residual water is detected on the object and subsequently the sterilant is injected into the container.

4 Claims, 22 Drawing Sheets

(51) Int. Cl.
    *A23B 5/02*     (2006.01)
    *A23B 7/02*     (2006.01)
    *A23B 9/08*     (2006.01)
    *A23L 3/34*     (2006.01)
    *A23L 3/015*     (2006.01)
    *A61L 2/20*     (2006.01)

(52) U.S. Cl.
    CPC .................................. *A23L 3/34* (2013.01); *A61L 2/16* (2013.01); *A23V 2002/00* (2013.01); *A61L 2/20* (2013.01); *A61L 2/24* (2013.01)

(58) Field of Classification Search
    USPC ........................................................ 422/28
    See application file for complete search history.

(56) References Cited

U.S. PATENT DOCUMENTS

| | | |
|---|---|---|
| 5,656,238 A | 8/1997 | Spencer et al. |
| 5,961,922 A | 10/1999 | Witte et al. |
| 6,060,019 A | 5/2000 | Spencer et al. |
| 6,365,102 B1 | 4/2002 | Wu et al. |
| 2006/0280646 A1* | 12/2006 | Shiosawa ............... A61L 2/02 422/23 |
| 2007/0065335 A1* | 3/2007 | Bedard ............... A61L 2/202 422/27 |
| 2008/0233002 A1 | 9/2008 | Mizuno et al. |
| 2010/0313441 A1* | 12/2010 | McLaren ............... F26B 5/04 34/403 |
| 2010/0316527 A1 | 12/2010 | McLaren et al. |

FOREIGN PATENT DOCUMENTS

| | | |
|---|---|---|
| JP | 8-206181 A | 8/1996 |
| JP | 10-216205 A | 8/1998 |
| JP | 2006-204889 A | 8/2006 |
| JP | 4526649 B2 | 6/2010 |

OTHER PUBLICATIONS

R. Yoshida et al., "Hydrogen Peroxide Vapour in the Proximity of Hydrogen Peroxide Sterilisers", Jpn J Environment Infect, 2011, pp. 239-242, vol. 26, No. 4.

Chinese Official Action issued in corresponding Chinese Patent Application No. 201380050042.X, dated Aug. 8, 2016, with English translation (9 pages).

Extended European Search Report issued in corresponding European Patent Application No. 13840965.1, dated Aug. 19, 2016 (9 pages).

Second Office Action dated Jun. 7, 2017 in corresponding Chinese Patent Application No. 201380050042.X, and a partial English translation thereof (10 pages).

\* cited by examiner

STERILIZATION METHOD AND STERILIZER

TECHNICAL FIELD

The present invention relates to a method for sterilizing an object under pressure within a container using a sterilant and a sterilizer using the method.

BACKGROUND ART

Conventional well-known method for sterilizing an object such as medical instrument includes applying heat or pressure from a source of high pressure steam, dry heat, electromagnetic radiation, hydrogen peroxide, gas plasma, or EOG gas.

The conventional method may be inapplicable to the object which can be damaged by heat or pressure. For example, the high pressure steam or the high temperature dry heat may be inapplicable to some objects. Also, the electromagnetic radiation may be inapplicable to other objects such as hollow metal or plastic composite material. Although the EOG gas sterilization may be applicable to any object irrespective of its material, it needs a considerable time for aeration procedures for the purpose of toxicity removal, which decreases the operational availability of the practical sterilizer.

One conventional solution that may solve those problems is a gas plasma sterilization method. For example, the method uses a sterilant containing hydrogen peroxide which is brought into contact with every surface portion of the object which has been washed and then dried completely. One known drying technique which may be used in the plasma gas sterilization is placing the object in a sterilization container, decompressing the interior of the container to vaporize residual water on the object, and then pumping to exhaust the generated vapor into the atmosphere and thereby to dry the object and the interior of the container.

Patent Document 1, for example, discloses a sterilization method using the technique, in which the interior of the object containing container is decompressed to about 40 to 200 Pa which is considered to be most advantageous for the generation of plasma within the container to vaporize the residual water on the object. Specifically, in this process, the vaporization of the residual water on the object loses its calories. Then, the object is heated at the generation of plasma within the interior of the container at a reduced pressure of about 40 to 200 Pa. Further, heat is transferred from the high-temperature container to the object through air introduced at the restoring of the pressure in the container to an atmospheric pressure or a quasi-atmospheric pressure (pressure which is close to the atmospheric pressure), increasing the temperature of the object and the residual water. Subsequently, a process for depressurizing the interior of the container to about 40 to 133 Pa and thereby to vaporize the residual water on the object is repeated at least twice.

PRIOR ART DOCUMENTS

Patent Documents

Patent Document 1: JP 4526649 B2

Non-Patent Documents

Non-patent Document 1: Rika YOSHIDA et al, "Hydrogen Peroxide Vapour in the Proximity of Hydrogen Peroxide Sterilisers", Jpn J Environment Infect, vol. 26, no. 4; p 239-242, 2011

SUMMARY OF INVENTION

Problems to be Solved by the Invention

Practically, however, there may be some cases in which the object not completely dried after pre-washing is fed into the plasma sterilization device. In this instance, the residual water disadvantageously blocks the sterilant from reaching the details of the object, which may cause incomplete sterilization of the object. Also, the sterilant may be absorbed in the residual water to remain on the object, which has been considered to affect the user's health (Non-Patent Document 1). As above, to remove the residual sterilant is one of the drawbacks which should be solved practically.

Another problem associated with the plasma gas sterilization may be that the residual water in the sterilization container loses its calories due to its vaporization caused at the drying of the object, which may provide an adverse effect on the drying of the object by the decompression boiling.

Indeed, the above-described drying technique employed in the conventional sterilization method using the agent may be effective for the objects with little residual water and without deep concaved portion. For the objects with a considerable amount of residual water and with deep concaved portions, however, the water retained in the deep concaved portions may be extracted therefrom and vaporized in the course of the first decompressing process. During this process, the pressure in the container is reduced to less than about 670 Pa, most preferably about 40 to 200 Pa to vaporize the residual water. Disadvantageously, some water may not be vaporized to remain on the object even in a pressure less than the triple point of water, i.e., 610 Pa. Under such pressure, the temperature of the residual water is less than its freezing point, causing the water to freeze into ice which may block the residual water in the concaved portions from being evaporated to remain on the object.

The above sterilization method decompresses, without interruption, the interior of the container to about 40 to 200 Pa which is most preferable for the plasma generation, through the triple point of water, which may freeze the residual water presenting in the concaved portions or at their entrances. Therefore, the incoming air which is introduced into the container for recovering the pressure in the container to the atmospheric pressure or quasi-atmospheric pressure may not be served for heating the object because it is blocked by the frozen water presenting in the concaved portions or at their entrances, which in turn result in an insufficient drying of the object.

Accordingly, a major object of the invention is to increase a contact efficiency of the sterilant in the sterilization process in which the interior of the container is decompressed and thereby to sterilize the object by the contact with the introduced sterilant, and to minimize or eliminate a residual sterilant in the container after the sterilization process.

Solution to Problem

A first aspect of the present invention relates to a method for sterilizing an object in a container using a sterilant, the method including the steps of:
(A1) decreasing a pressure in a container to a first pressure which is equal to or more than the triple point pressure of water;
(A2) maintaining the first pressure in the container;
(A3) increasing the pressure in the container to a second pressure which is equal to or close to an atmospheric pressure;
(A4) decreasing the pressure in the container to a third pressure which is substantially equal to or less than the first pressure; and
(A5) injecting the sterilant into the container.

Further, the method according to the first aspect of the present invention may further include comprising the step (A6) of determining whether residual water exists in the container after the step (A2), wherein the steps (A3), (A1), (A2) and (A6) are performed in this order if it is determined in the step (A6) that the residual water exists, and wherein the steps (A4) and (A5) are performed in this order if it is determined in the step (A6) that the residual water does not exist.

In the method according to the first aspect of the present invention, whether the residual water exists may be determined in the step (A6) based on an actual time in which the pressure in the container is decreased to the first pressure. Also, the step (A6) may comprise comparing a reference time stored in a memory and the actual time, and wherein, if the actual time is equal to or less than the reference time, it is determined that no residual water exists.

A second aspect of the present invention relates to a method for sterilizing an object in a container using a sterilant, the method including the steps of:
(B1) decreasing a pressure in a container to a first pressure which is equal to or more than the triple point pressure of water;
(B2) after the pressure in the container is reduced to the first pressure, inhibiting a pressure increase or decrease operation for a certain period of time;
(B3) increasing the pressure in the container to a second pressure which is equal to or close to an atmospheric pressure;
(B4) decreasing the pressure in the container to a third pressure which is substantially equal to or less than the first pressure;
(B5) injecting the sterilant into the container; and
(B6) determining whether residual water exists in the container after the step (B2),
    wherein the steps (B3), (B1), (B2) and (B6) are performed in this order if it is determined in the step (B6) that the residual water exists, and wherein the steps (B4) and (B5) are performed in this order if it is determined in the step (B6) that the residual water does not exist.

In the method according to the second aspect of the present invention, whether the residual water exists in the container may be determined in the step (B6) based on a rate of pressure increase per unit time in the step (B2).

In the method according to the second aspect of the present invention, the step (B6) may include comparing a reference rate of pressure increase stored in a memory and the actual rate of pressure increase, and wherein, if the actual rate of pressure increase is equal to or less than the reference rate of pressure increase, it is determined that no residual water exists.

A third aspect of the present invention relates to a sterilizer for sterilizing an object in a container using a sterilant, the sterilizer including:
(C1) a pressure controller having a mechanism for decreasing a pressure in the container from an atmospheric pressure or a quasi-atmospheric pressure to a predetermined pressure, a mechanism for maintaining the predetermined pressure, and a mechanism for increasing the pressure in the container to the atmospheric pressure or the quasi-atmospheric pressure;
(C2) a sterilant injector for injecting a sterilant into the container;
(C3) a pressure measuring unit for measuring the pressure in the container;
(C4) a determining section for determining an existence of residual water in the container as the pressure maintaining mechanism maintains the triple point pressure of water or higher in the container;
(C5) a memory for memorizing a reference time required for decreasing the pressure in the container from the atmospheric pressure or the quasi-atmospheric pressure to the predetermined pressure;
(C6) a time measurement unit for measuring an actual time required for decreasing the pressure in the container from the atmospheric pressure or the quasi-atmospheric pressure to the predetermined pressure;
(C7) a calculator for calculating a difference between a time in decreasing the pressure in the container from the atmospheric pressure to the predetermined pressure and a time decreasing the pressure in the container from the quasi-atmospheric pressure to the predetermined pressure;
(C8) a comparator for comparing the reference time stored in the memory and the actual time measured by the time measurement unit;
(C9) a determining unit for determining a quantity of the residual water in the container based on a result made by the comparator.

A fourth aspect of the present invention relates to a sterilizer for sterilizing an object in a container using a sterilant, the sterilizer including:
(D1) a pressure controller having a mechanism for decreasing a pressure in the container from an atmospheric pressure or a quasi-atmospheric pressure to a predetermined pressure, and a mechanism for increasing the pressure in the container to the atmospheric pressure or the quasi-atmospheric pressure;
(D2) a sterilant injector for injecting a sterilant into the container;
(D3) a pressure measuring unit for measuring the pressure in the container;
(D4) a determining section for determining an existence of residual water in the container after the elapse of a certain period of time from the point when the pressure in the container is decreased to the triple point pressure of water or higher;
(D5) a memory for storing a reference rate of pressure increase used when the pressure control is stopped for a certain period of time after the pressure is decreased from the atmospheric pressure or the quasi-atmospheric pressure to the predetermined pressure;
(D6) a pressure increasing rate determining unit for determining an actual rate of pressure increase while the pressure control is stopped for a certain period of time after the pressure is decreased from the atmospheric pressure or the quasi-atmospheric pressure to the predetermined pressure;

(D7) a calculator for calculating the rate of pressure increase while the pressure control is stopped for a certain period of time after the pressure is decreased;

(D8) a comparator for comparing the reference rate of pressure increase stored in the memory and the actual rate of pressure increase measured by the time measurement unit;

(D9) a determining unit for determining a quantity of the residual water in the container based on a result made by the comparator.

One aspect of the present invention relates to a method for sterilizing an object in a container using a sterilant, the method comprising the steps of:

decreasing a pressure in a container to a first pressure which is equal to or more than the triple point pressure of water;

after an elapse of a certain period of time, decreasing the pressure in the container to a third pressure which is equal to or less than the triple point pressure of water; and injecting a sterilant into the container.

As such, the method according to the present invention enables the residual water, which is impregnated onto the object to be sterilized during the pre-washing, to be efficiently and certainly drained away before the sterilant injection. Further, the method enables the residual water to be drained away while the pressure is maintained which is equal to or higher than the triple point pressure at which water freezes, during the pressure decreasing process, thereby determining the existence of the residual water. If the residual water exists, the pressure in the container, is increased to the atmospheric pressure or the quasi-atmospheric pressure and the object is heated to drain away the residual water. Further, these steps are repeated until that the object does not include the residual water thereon is determined, the pressure is decreased to a pressure which is lower than the triple point pressure at which water freezes and subsequently the sterilant is injected into the container for sterilization.

Advantageous Effects of Invention

According to the first aspect of the present invention, the pressure increasing/decreasing process is repeated between the atmospheric pressure (or the quasi-atmospheric pressure) and the pressure which is equal to or higher than the triple point pressure of water for the purpose of drying the inside of the container which accommodates the object to be sterilized therein, the period of time required for the pressure decreasing process is used to determine the inside of the container is adequately dried, and subsequently the pressure is decreased to the pressure which is lower than the triple point pressure to inject the sterilant into the container, thereby increasing the contact efficiency of the sterilant and minimizing or eliminating the residual sterilant in the container after the sterilization process.

The reference time for decreasing the pressure is used to determine the inside of the container is adequately dried and thereby to determine the existence of the residual water without complete measurements and/or calculations, in a case where the same instruments are used.

According to the second aspect of the present invention, the pressure increasing/decreasing process is repeated between the atmospheric pressure (or the quasi-atmospheric pressure) and the pressure which is equal to or higher than the triple point pressure of water for the purpose of drying the inside of the container which accommodates the object to be sterilized therein, the actual rate of pressure increase measured while the pressure increases in the step of inhibiting a pressure increase or decrease operation may be compared with the reference rate to determine the inside of the container is adequately dried, and subsequently the pressure is decreased to the pressure which is lower than the triple point pressure to inject the sterilant into the container, thereby increasing the contact efficiency of the sterilant and minimizing or eliminating the residual sterilant in the container after the sterilization process.

The reference rate of pressure increase is used to determine the inside of the container is adequately dried and thereby to determine the existence of the residual water without complete measurements and/or calculations, in a case where the same instruments are used and free of influence from the operating condition of a pump used for decreasing the pressure.

According to the third aspect of the present invention, the pressure increasing/decreasing process is repeated between the atmospheric pressure (or the quasi-atmospheric pressure) and the pressure which is equal to or higher than the triple point pressure of water for the purpose of drying the inside of the container which accommodates the object to be sterilized therein, the period of time required for the pressure decreasing process is used to determine the inside of the container is adequately dried, and subsequently the pressure is decreased to the pressure which is lower than the triple point pressure to inject the sterilant into the container, thereby increasing the contact efficiency of the sterilant and minimizing or eliminating the residual sterilant in the container after the sterilization process.

The apparatus according to the third aspect of the present invention enables the residual water, which is impregnated onto the object to be sterilized during the pre-washing, to be efficiently and certainly drained away before the sterilant injection. This enables the drying process with a shorter time without any heating process or the heated gas and thereby the gas can be used for drying the object which can be damaged by heat or pressure without causing any problems. Further, the apparatus does not require an inflowing means for inflowing warm or hot air into the container, avoiding causing the system of the sterilizer in its entirety become complicated and/or huge.

According to the fourth aspect of the present invention, the pressure increasing/decreasing process is repeated between the atmospheric pressure (or the quasi-atmospheric pressure) and the pressure which is equal to or higher than the triple point pressure of water for the purpose of drying the inside of the container which accommodates the object to be sterilized therein, the actual rate of pressure increase measured while the pressure increases in the step of inhibiting a pressure increase or decrease operation may be compared with the reference rate to determine the inside of the container is adequately dried, and subsequently the pressure is decreased to the pressure which is lower than the triple point pressure to inject the sterilant into the container, thereby increasing the contact efficiency of the sterilant and minimizing or eliminating the residual sterilant in the container after the sterilization process.

The apparatus according to the fourth aspect of the present invention enables the residual water, which is impregnated onto the object to be sterilized during the pre-washing, to be efficiently and certainly drained away before the sterilant injection. This enables the drying process with a shorter time without any heating process or the heated gas and thereby the gas can be used for drying the object which can be damaged by heat or pressure without causing any problems. Further, the apparatus does not require an inflowing means for inflowing warm or hot air into the container, avoiding causing the system of the sterilizer in its entirety become complicated and/or huge.

DESCRIPTION OF EMBODIMENTS

Referring to the accompanying drawings, several embodiments of the invention will be described in detail below, by which objects such as medical instruments including tweezers, scissors, forceps and catheter and a sterilant are sterilized by using peracid such as hydrogen peroxide and peracetic acid. In the following descriptions, directional terminologies, such as "upper", "lower", "left", "right", "front", "rear", others combined terminologies thereof, "clockwise" and "counterclockwise" are used for the better understanding of the invention with reference to the drawings and should not be used to restrict the invention.

Figure 1:
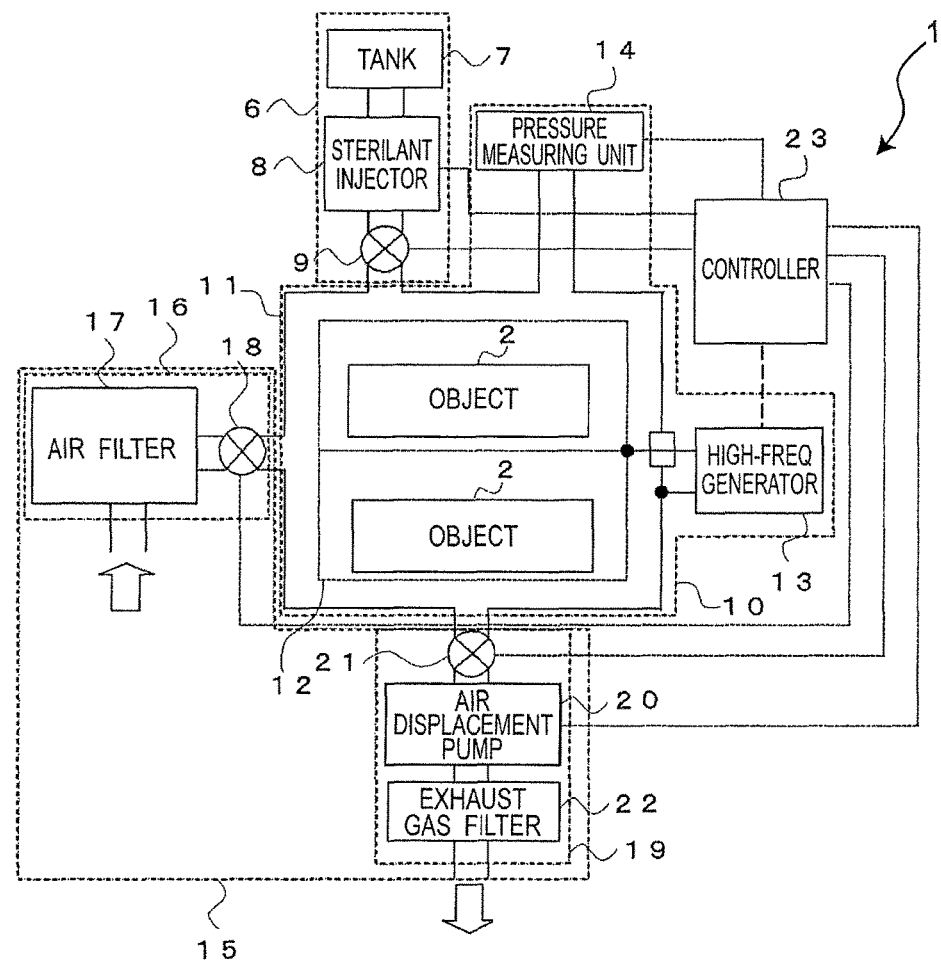
FIG. 1 is a block diagram schematically showing a sterilizer in its entirety according to an embodiment of the present invention.

FIG. 1 is a block diagram schematically showing a sterilizer in its entirety according to an embodiment of, the present invention. The sterilizer 1, which is referred to as simply "apparatus" as necessary, is designed to sterilize the object 2 by using a sterilant within an adequately decompressed container 11. As shown in FIG. 1, the sterilizer 1 includes a sterilant supply system 6, a sterilization system 10, an intake/exhaust piping system 15 for controlling an air into and out of the container 11, and a controller 23 which controls the sterilizer 1 in its entirety.

The sterilant supply system 6 includes a tank 7 which reserves the sterilant, a sterilant injector 8, and a sterilant injection solenoid valve 9. The sterilant injector 8 is configured to measure an appropriate quantity of the sterilant to supply it into the container 11 after the solenoid valve 9 is opened in response to a control signal from the controller 23.

The sterilization system 10 includes the container 11 having an internal box 12 mounted therein for accommodating the object 2 to be sterilized. The system 10 further includes a high-frequency generator 13 provided outside the container 11 for generating plasma within an interior of the container 11, and a pressure measuring unit 14 for measuring a pressure in the container 11. The container 11 is fluidly connected to the sterilant supply system 6 and the intake/exhaust piping system 15.

The container 11 and its internal box 12 are each made of electrically conductive material having a certain strength, stiffness and corrosion resistance. The container 11 and the internal box 12 are electrically insulated each other. The container 11 serving as an external box and the internal box 12 each may be made of a metal plate such as a steel plate. The container or external box 11 is formed by bending and machining a commonly-used metal plate to form the airtightly sealable interior inside the internal box. The internal box 12 is formed by bending and machining a perforated metal plate or a metal plate having many perforations so that the vaporized sterilant or fluid such as air or gaseous plasma can freely move between the interior and the exterior of the internal box 12.

The high-frequency generator 13, which serves as a plasma generator, is disposed outside of the container 11. The high-frequency generator 13 may include a high-frequency circuit and a high-frequency power source. The high-frequency generator 13, which has one part/end which is electrically connected to the container or external box 11 and the other part/end which is electrically connected to the internal box 12 via a conventional vacuum sleeve, is configured so that, when activated, it generates plasma within a space formed between the container or external box 11 and the internal box 12.

The intake/exhaust piping system 15 includes an intake piping system 16 through which an atmospheric air is introduced into the container 11 and an exhaust piping system 19 through which the air in the container 11 is exhausted to the outside thereof. The intake piping system 16 includes an air filter 17 which purifies the atmospheric air when it is introduced into the container 11 and an introduction solenoid valve 18 which is opened for the introduction of the atmospheric air. The exhaust piping system 19 includes an air displacement pump 20 which evacuates the container 11, and a solenoid valve 21 which is opened for the evacuation.

This arrangement allows that the atmospheric air is cleaned by the air filter 17 located at the upstream side of the solenoid valve 18 as it is introduced into the container 11 in response to a control signal from the controller 23. Likewise, the atmosphere in the container 11 is cleaned by an exhaust gas filter 22 located at the downstream side of the air displacement pump 20 as it is evacuated in response to a control signal from the controller 23.

The controller 23, which controls the sterilizer 1 in its entirety, has a microcomputer as a main component. The controller 23 may be mounted on a control panel (not shown). As shown in FIG. 1, the sterilant injector 8 and the solenoid valve 9 in the sterilant supply system 6, the high-frequency generator 13 and the pressure measuring unit 14 in the sterilization system 10, the solenoid valve for introducing the atmospheric air 18, the air displacement pump 20 and the solenoid valve 21 in the intake/exhaust piping system 15 are each connected for signal transmission and reception to the controller 23 so that they are controlled by control signals received from the controller 23. Each of the solenoid valves 9, 18 and 21 may be any one of conventional electromagnetic control valves.

Figure 2:
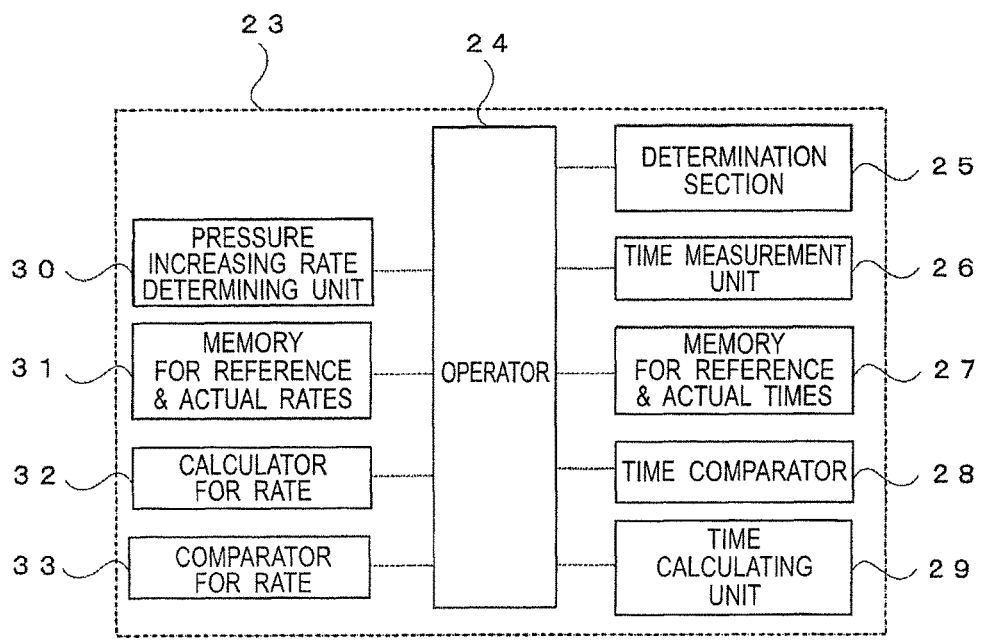
FIG. 2 is a block diagram showing the controller of the sterilizer shown in FIG. 1 in detail.

The controller 23 will be described in detail below. FIG. 2 is a block diagram showing the controller 23 of the sterilizer 1 shown in FIG. 1 in detail. In the description below, pressures and temperatures are denoted by reference signs such as P101, T101 illustrated in FIGS. 5 to 8 and FIGS. 13 to 16 for the better understanding of the operation.

As shown in FIG. 2, the controller 23 of the sterilizer 1 includes a residual water determining unit/section 25 which determines the existence of a residual water, a time measurement unit 26 which measures an actual time T101 spent for decreasing the pressure in the container to a predetermined first pressure P101, a memory 27 which stores a reference time T101a which is a reference value for decreasing the pressure to the first pressure P101 and the actual time T101, and a time comparator 28 which compares the actual time T101 with the reference time T101a stored in the memory 27. The units 25 to 28 are connected for signal transmission and reception to the operator 24.

The period of time T101a, which is the reference time for decreasing the pressure in the container 11 to the first pressure P101, corresponds to a period of time for decreasing the pressure in the container 11 to the first pressure P101 in the pressure decreasing step 101a described below when no residual water is detected on the object 2.

The controller 23 includes a time calculating unit 29 which calculates a time difference in the pressure decrease, stored in the memory 27, which may be caused due to the variation of the first pressure P101, a pressure increasing rate determining unit 30 which measures a rate of pressure increase from the first pressure P101, a memory 31 which stores a reference rate of pressure increase Rp114a and an actual rate of pressure increase Rp114, a calculator 32 which calculates a rate of pressure increase per unit time, and a comparator 33 which compares the reference rate of pressure increase Rp114a with the actual rate of pressure increase Rp114. The units 29 to 33 are connected for signal transmission and reception to the operator 24.

As described below, the reference rate of pressure increase Rp114a is a reference value for increasing the pressure from the first pressure P101. The reference rate of pressure increase Rp114a further corresponds to a rate of pressure increase for increasing the pressure from the first pressure P101 when no residual water is detected on the object 2 to be sterilized.

Figure 3A:
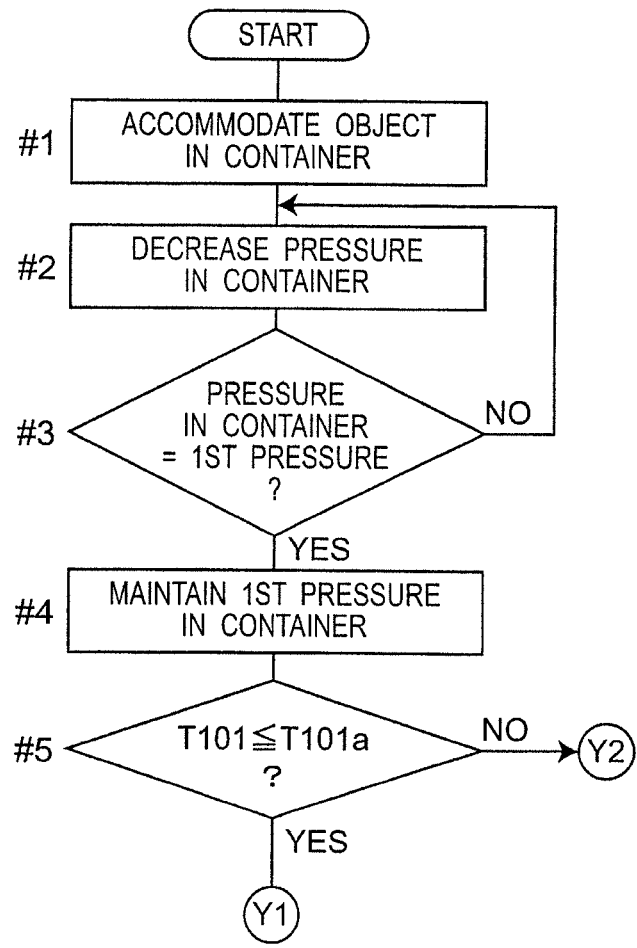
FIGS. 3A to 3C are flowcharts illustrating a method for controlling the sterilizer according to the first embodiment of the present invention.
Figure 3B:
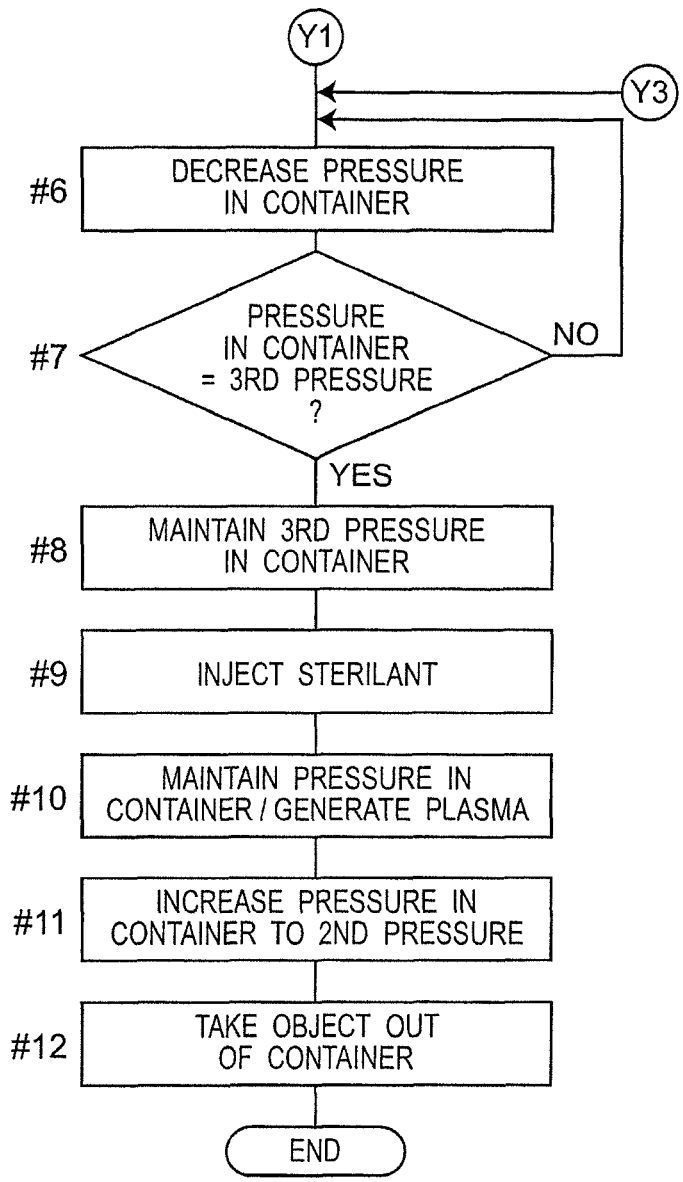
Figure 3C:
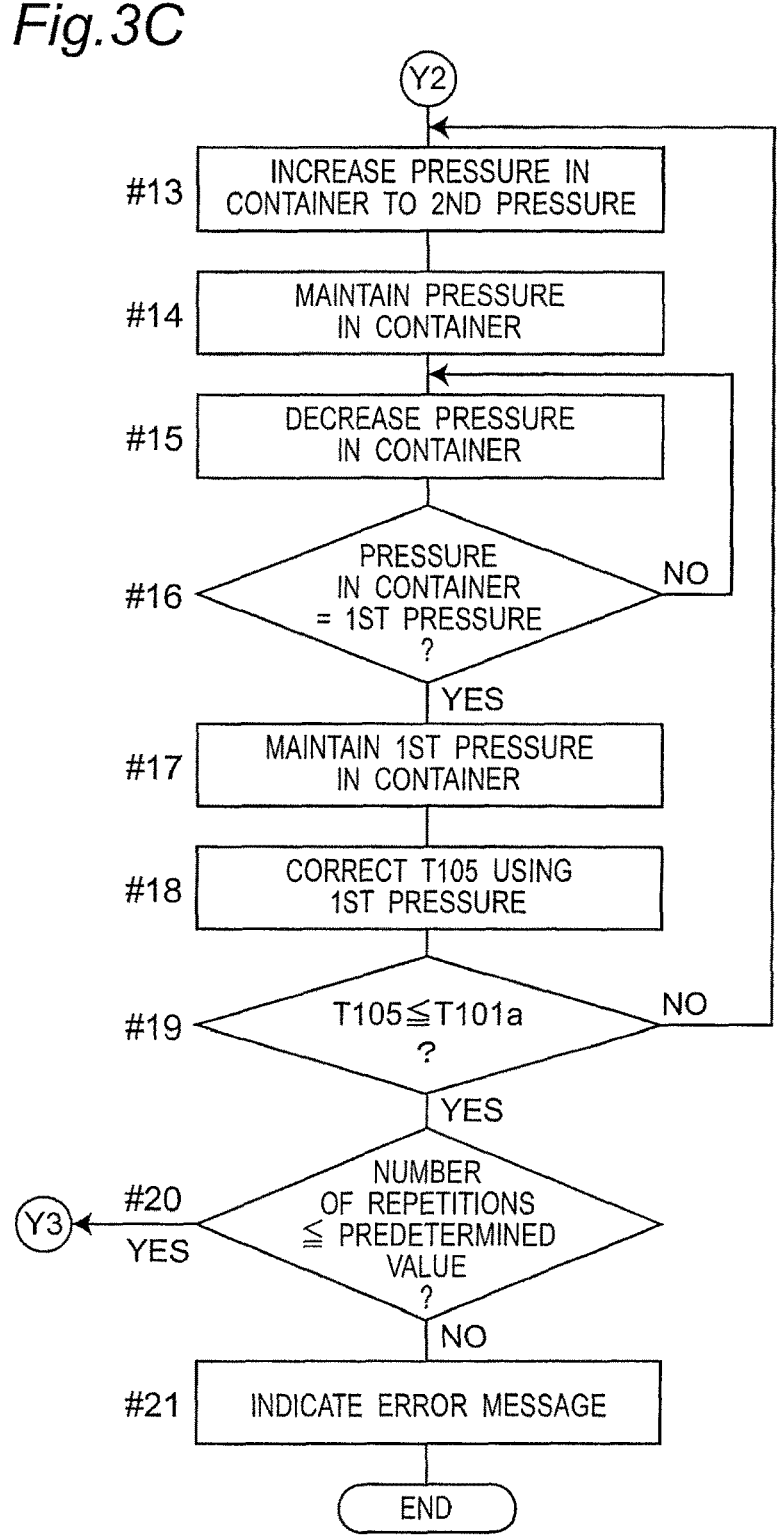

Descriptions will be made to the operation and control of the sterilizer 1 so constructed. FIGS. 3A to 3C are flowcharts illustrating the operation of the sterilizer according to the first embodiment of the present invention. As illustrated in FIG. 3A, before driving the sterilization system, in step #1 the object 2 to be sterilized is accommodated in the internal box 12 of the container 11. In step #2, the air displacement pump 20 is energized to decrease the pressure in the container 11. Then, in step #3, a determination is made whether the pressure in the container 11 reaches the first pressure P101 which is equal to or higher than the triple point pressure of water.

The pressure in the container 11 is measured by the pressure measuring unit 14, and the measurement is transmitted to the controller 23. Based on the output signal from the operator 24 of the controller 23, the displacement pump 20 and the solenoid valve 21 are controlled so that the pressure in the container 11 is decreased to the target pressure, i.e., the first pressure P101. If it is determined that the pressure in the container 11 reaches the first pressure P101, the pressure in the container 11 is maintained at the first pressure P101 for a certain period of time.

The time measurement unit 26 measures the actual time T101 required for the pressure in the container to reach the first pressure P101 from the beginning of the pressure reduction control. The measured actual time T101 is stored in the memory 27. Also, the air displacement pump 20 is deactivated and the solenoid valve 21 is closed, for a certain period of time. Then, in step #4, as described above, the air displacement pump 20 is activated again and the solenoid valve 21 is controlled so that the pressure in the container 11 is maintained at the first pressure P101 for a certain period of time T102.

After the elapse of the time T102, in step #5 a comparison is made between the reference time T101a stored in the memory 27 and the actual time. As described above, the reference time T101a is the reference value for decreasing the pressure in the container 11 to the first pressure P101 and corresponds to a period of time for decreasing the pressure in the container 11 to the first pressure P101 when no residual water is detected on the object 2 in the pressure decreasing step 101a. The actual time T101 is the period of time for actually decreasing the pressure in the container 11 to the first pressure P101.

In order to properly compare the actual time T101 and the reference time T101a at the comparator 28, the actual time T101 and the reference time T101a are adjusted by using a difference between the pressures inside and outside the container at the beginning of the pressure decreasing operation at the time calculating unit 29. Then, the determination section 25 uses the adjusted time to determine whether T101 is equal to or less than T101a, i.e., T101 T101a. The result is used to determine the existence of residual water on the object 2 to be sterilized.

If it is determined in step #5 that no residual water exists on the object 2, the displacement pump 20 and the solenoid valve 21 are controlled to decrease the pressure in the container 11. If it is determined in step #7 that the pressure in the container 11 is decreased to the third pressure P103 which is lower than the triple point pressure of water, the pressure in the third pressure in the container 11 is maintained at the third pressure for a certain period of time. After the elapse of the time, in step #9 the sterilant is injected into the container 11. The condition in the container 11 is maintained for a certain period of time, and then plasma is generated within the container 11 in step #10. Then, in step #11 the pressure in the container 11 is increased to the second pressure P102. Next, in step #12 the object 2 is removed from the container 11 to terminate the sterilization step.

If it is determined in step #5 that T101 is greater than T101a, i.e. the residual water is detected on the object 2 to be sterilized (step #5: NO), in step #13 the pressure in the container 11 is increased to the second pressure P102. In step #14, the pressure in the container 11 is maintained at the second pressure for a certain period of time. Then, steps #15 to #19 are repeated, which correspond to steps #2 to #5, respectively.

If it is determined in step #19 that the T105 is equal to or less than T101a, namely, no residual water exists on the object 2, a determination is made in step #20 whether the number of times repeating the steps #15 to #19 is less than a predetermined value. If it is determined in step #20 that the number of repetitions is less than the predetermined value, the steps #6 to #12 are performed and then the sterilization process is terminated. If on the other hand it is determined in step #20 that the number of repetitions is greater than the predetermined value (if NO), an error message is indicated on the display (not shown) to turn off the system in step #21.

Figure 4A:
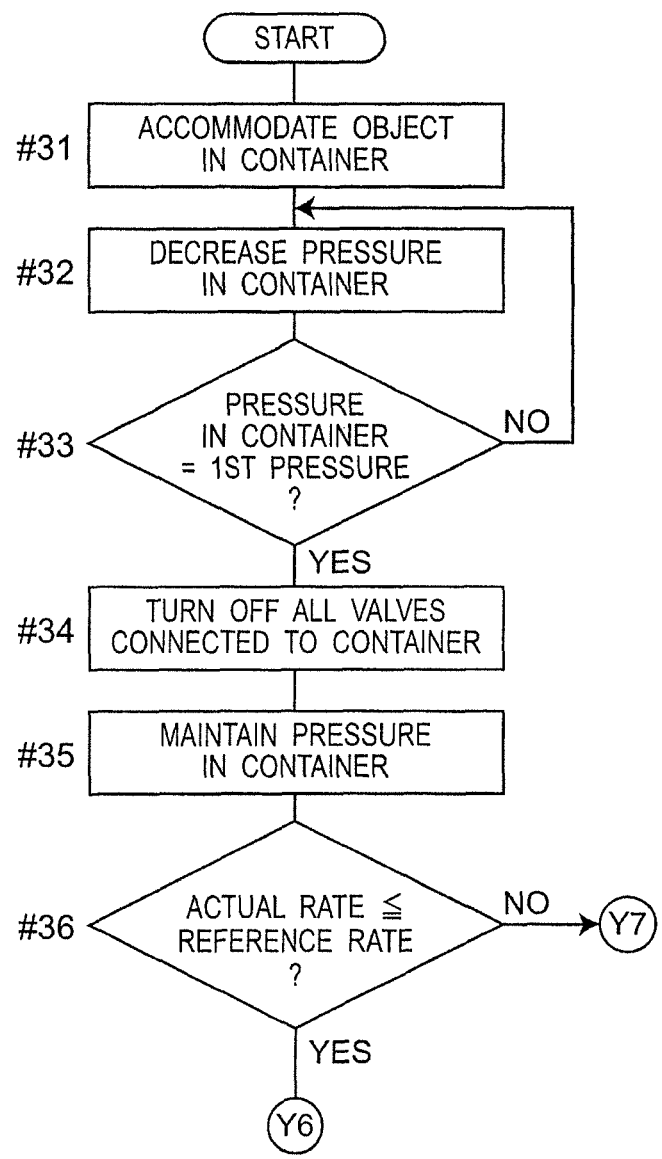
FIGS. 4A to 4C are flowcharts illustrating a method for controlling the sterilizer according to the second embodiment of the present invention.
Figure 4B:
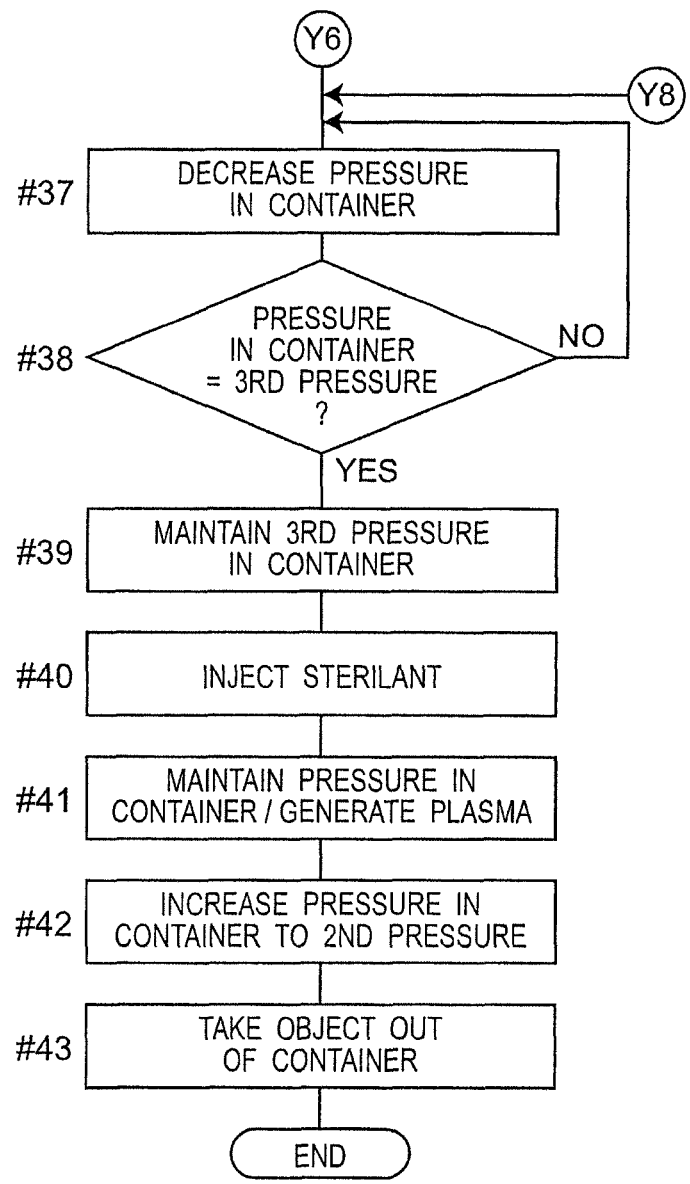
Figure 4C:
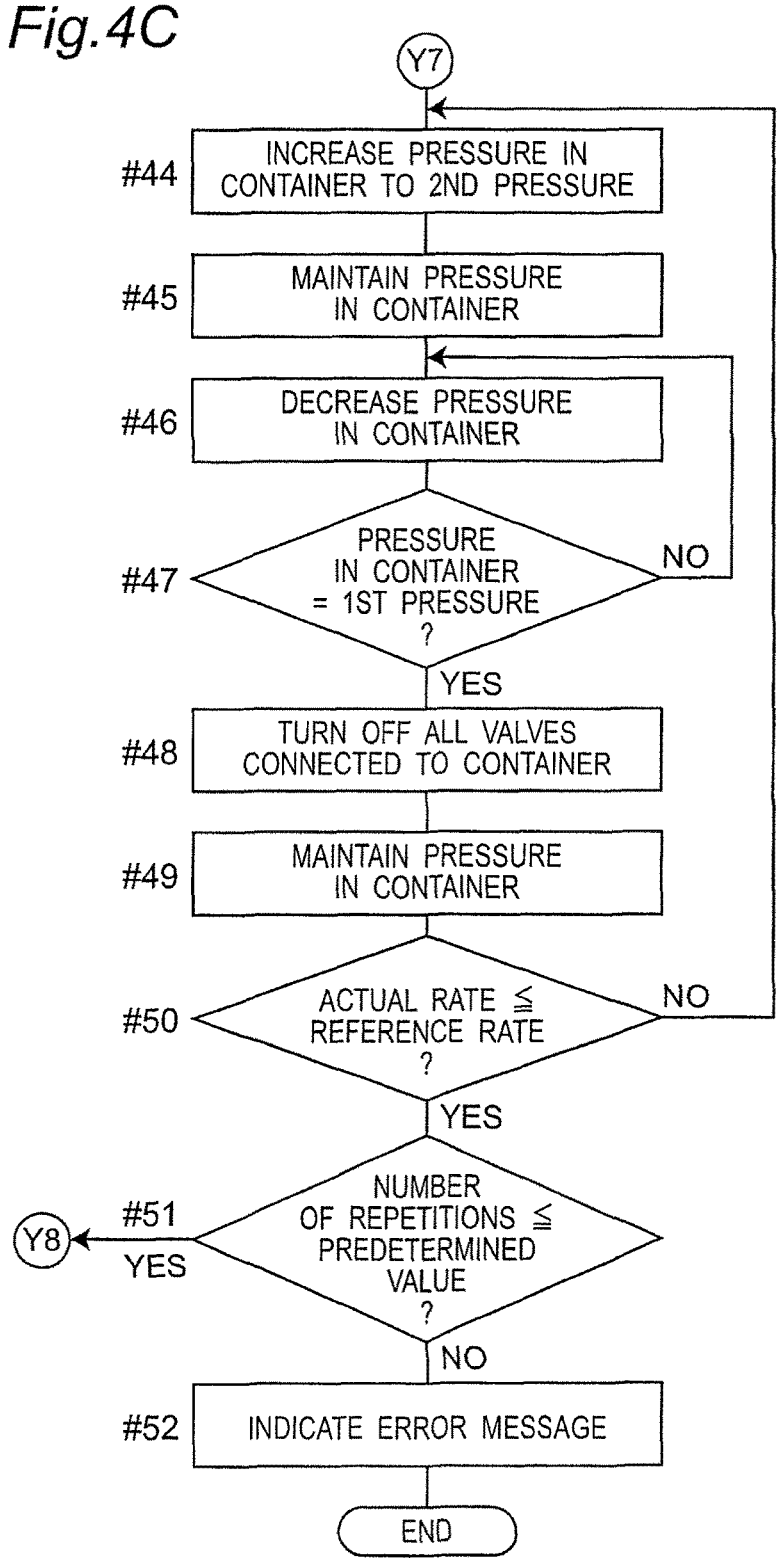

Next, descriptions will be made to the operation and control of the sterilizer according to the second embodiment of the invention with reference to flowcharts shown in FIGS. 4A to 4C. As illustrated in FIG. 4A, before driving the sterilization system, in step #31, the object 2 to be sterilized is accommodated in the internal box 12 of the container 11. In step #32, the air displacement pump 20 is energized to decrease the pressure in the container 11. Then, in step #33, a determination is made whether the pressure in the container 11 reaches the first pressure P101 which is equal to or higher than the triple point pressure of water.

The pressure in the container 11 is measured by the pressure measuring unit 14, and the measurement is transmitted to the controller 23. Based on the output signal from the operator 24 of the controller 23, the displacement pump 20 and the solenoid valve 21 are controlled so that the pressure in the container 11 is decreased to the target pressure, i.e., the first pressure P101. If it is determined that the pressure in the container 11 reaches the first pressure P101, the solenoid valves 9, 18, and 21 connected to the container 11 are closed in step #34.

The pressure measuring unit 14 continues to measure the pressure inside the container, and the time measurement unit 26 is activated to measure a period of time elapsed T102. After the first pressure P101 is maintained in the container 11 for the certain period of time T102 in step #35, a pressure difference between the first pressure P101 and the pressure measured after the elapse of the time T102 is obtained by the pressure increasing rate determining unit 30. The pressure difference and the period of time T102 are used to calculate an actual rate of pressure increase Rp114 by means of the calculator 32. The calculation result is temporarily stored in the memory 31. The memory 31 stores a reference rate of pressure increase Rp114a.

In the next step #36, a difference between the actual rate of pressure increase Rp114 and the reference rate of pressure increase Rp114a, both stored in the memory 31, is calculated and, based on the result, it is determined by the comparator 33 whether the actual rate of pressure increase Rp114 is equal to or less than the reference rate of pressure increase Rp114a. As described above, the reference rate of pressure increase Rp114a corresponds to the rate of pressure increase in the pressure increase operation from the first pressure P101 when no residual water exists. Accordingly, the existence of water on the object 2 can be determined by comparing the rates of increase Rp114 and Rp114a.

If it is determined in step #36 that the actual rate of pressure increase Rp114 is equal to or less than the reference rate of pressure increase Rp114a, namely, no residual water exists on the object 2, the displacement pump 20 and the solenoid valve 21 are controlled to decrease the pressure in the container 11 in step #38. If it is determined in step #39 that the pressure in the container 11 is decreased to the third pressure P103 which is lower than the triple point pressure of water, the pressure in the container 11 is controlled at the third pressure for a certain period of time. After the elapse of the time T102, in step #40 the sterilant is injected into the container 11. After the further elapse of a certain period of time during which the container 11 is maintained in the same condition, plasma is generated in the container 11 in step #41. Then, in step #42 the pressure in the container 11 is increased to the second pressure P102. In the next step #43, the object 2 is removed from the container 11 and the sterilization process is terminated.

If it is determined in step #36 that the actual rate of pressure increase Rp114 is greater than the reference rate of pressure increase Rp114a; namely, the residual water exists on the object 2, in step #44 the pressure in the container 11 is increased to the second pressure P102. Then, in the next step #45 the second pressure in the container 11 is maintained for a certain period of time. Then, steps #46 to #50 are repeated, which correspond to steps #32 to #36, respectively.

If it is determined in step #50 that the actual rate of pressure increase Rp114 is equal to or less than the reference rate of pressure increase Rp114a; namely, no residual water exists on the object 2, in step #51, a determination is made in step #51 whether the number of times repeating the steps #46 to #50 is less than a predetermined value. If it is determined in step #51 that the number of repetitions is less than the predetermined value, the steps #37 to #43 are performed and then the sterilization process is terminated. If on the other hand it is determined in step #51 that the number of repetitions is greater than the predetermined value, an error message is indicated on the display (not shown) to turn off the system in step #52.

For the first embodiment shown in FIGS. 3A to 3C, a relation between the sterilization time elapsed and the pressure in which no residual water exists on the object 2 will be described with reference to a graph shown in FIG. 5.

In a typical sterilization method in which an object to be sterilized is dried through the decompression drying technique, the pressure in the container 11 is decreased by the displacement pump 20 during which the residual water existing outside or inside the object 2 is evaporated. The residual water loses its calories as it is evaporated. This process is hereinafter referred to as "step 101".

According to this embodiment, in the pressure decreasing process in step 101 the pressure is decreased to the first pressure P101 which is higher than the triple point pressure of water. The first pressure P101 is equal to or higher than the triple point pressure of water (610 Pa) at which water freezes into ice. The first pressure P101 is preferably in the range between 610 and 2,000 Pa, more preferably between 670 and 1,000 Pa. In step 101 followed by step 102, the first pressure P101 in the container 11 is maintained for the period of time T102. In this step, heat is transferred from the object to the cold residual water, warming and thereby evaporating the residual water. The first pressure P101 is higher than the triple point pressure of water, 610 Pa, which ensures that the residual water does not freeze during step 102.

In step 102, the first pressure P101 in the container 11 is maintained through the opening/closing control of the solenoid valve 21 connected to the air displacement pump 20, in response to a control signal from the controller 23 and using the pressure measured by the pressure measuring unit 14. In one embodiment, the period of time T102 in step 102 may be equal to a period of time during which a half quantity of heat is transferred to the residual water. When the object 2 is a PTFE (fluororesin) tube having an outer diameter of 4 millimeters and an inner diameter of 2 millimeters for example, the period of time T102 is about 5 seconds. When the object 2 is a silicone tube having an outer diameter of 10 millimeters and an inner diameter of 5 millimeters, the certain period of time T102 is about 25 seconds.

In step 103 subsequent to step 102, the solenoid valve 18 is opened to allow the atmospheric air to inflow into the container 11 through the air filter 17. In the embodiment, in step 103 the pressure in the container 11 is increased to the second pressure P102 which is equal to the atmospheric pressure or quasi-atmospheric pressure which is close to the atmospheric pressure, thereby inflowing the atmospheric air having a higher temperature than that of the atmosphere in the container 11 into the container 11. The object 2 and the residual water are exposed to the atmospheric air, resulting in the increase of their temperatures.

In step 104 subsequent to step 103, the second pressure P102 is maintained in the container 11, and heat from the atmospheric air introduced in step 103 is transferred to the object 2 and the residual water. The period of time of step 104 may be determined as necessary. The object 2 and the residual water are heated in steps 103 and 104. As a result, at the beginning of step 105 subsequent to step 104 starts, the temperatures of the atmosphere in the container 11 and the object 2 in the container are higher than those at the end 112 of step 102, causing the decompression boiling of the residual water.

The drying process of steps 103, 104, 105 and 102 are repeated until it is determined at the end 11 of step 101 that no residual water exists in the container by the residual water determining section 25. If it is determined that no residual water exist at that point 111, the program proceeds to step 106 after the completion 112 of step 102 and then to step 107 in which the interior of the container 11 is maintained at the third pressure P103 which is equal to or less than the first pressure P101.

The third pressure P103 is an appropriate pressure for injecting the sterilant into the container 11 and for the generation of plasma. The third pressure P103 is preferably in a range between 30 and 200 Pa. The third pressure P103 is equal to or less than the triple point pressure of water (610 Pa), at which water freezes into ice. Because the previous drying process has removed the residual water, no freezing would occur on the object 2. For heating the container 11 or external box, internal box 12, and the object 2 in step 107, a high-frequency wave may be applied from the high-frequency generator 13 between the container 11 and the internal box 12 for the plasma generation.

At the end 108 of step 107, a predetermined quantity of the sterilant is injected via the solenoid valve 9 into the container 11 in the form of steam or vapor. In step 109, the sterilant injected in the container 11 passes through the perforations of the internal box and subsequently adheres to the object 2 for its sterilization. A certain period of time necessary for the effective sterilization is allocated to step 109. After step 109 is completed, the pressure in the container 11 is increased to the second pressure P102, terminating the first sterilization step. More preferably, step 109 is repeatedly performed, thereby ensuring the sterilization effect.

The period of time T101 necessary for decreasing the pressure to the first pressure P101 which is equal to or higher than the triple point pressure of water is measured at the time measurement unit 26 through the monitoring the output of the pressure measuring unit 14 after starting the operation by the sterilization system. The period of time T101 spent for step 101 has a relationship with a quantity of the residual water existing on the object 2 in which the period of time T101 increases with the quantity of the residual water.

Figure 5:
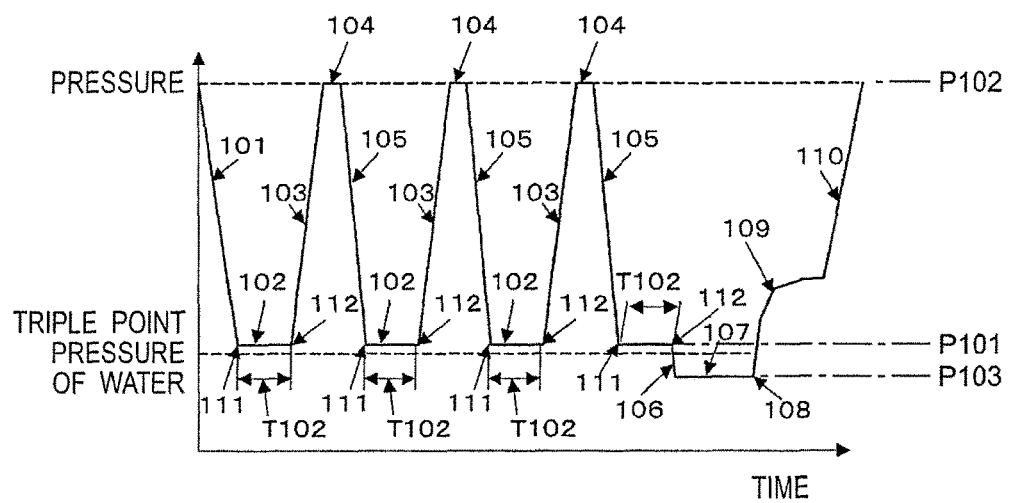
FIG. 5 is a graph showing the pressure in the container as time in the sterilization process according to the first embodiment of the present invention
Figure 6:
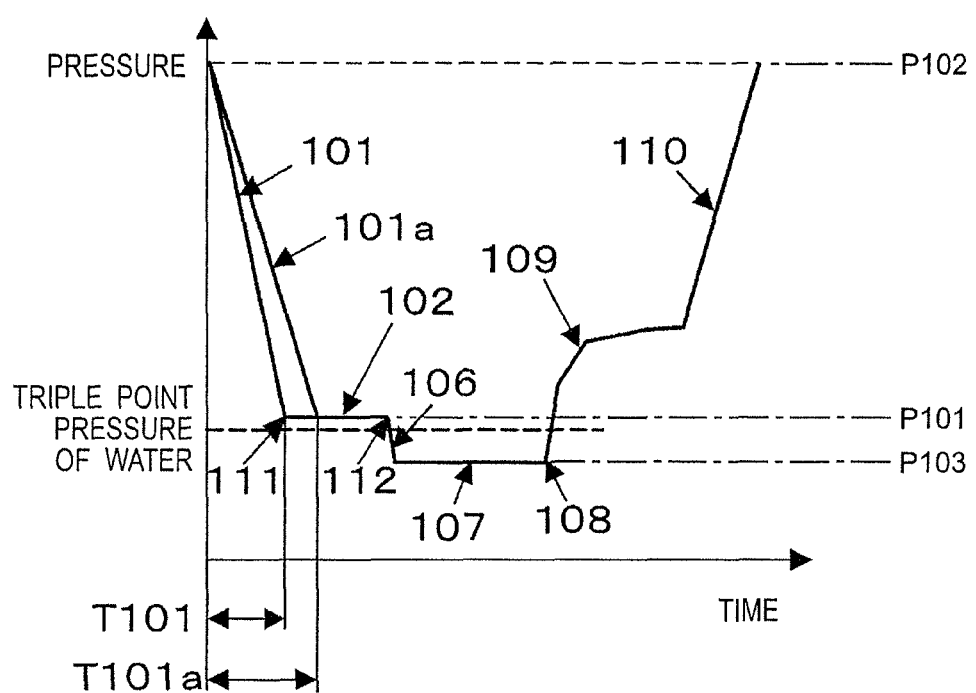
FIG. 6 is a partial enlarged view of the graph in FIG. 5 showing an embodiment in which no residual water is detected.

FIG. 6 is a partial enlarged view of the graph in FIG. 5 showing an embodiment in which no residual water is detected by the determining section 25. In the series of processes shown in FIG. 6, it is determined in step 101a whether there exists the residual water on the object and, if it is determined that no residual water exists, the period of time T101a necessary for decreasing the pressure down to the first pressure P101 (i.e., reference time) is stored in the memory 27.

If it is determined that the actual time T101 is equal to or less than the reference time 101a, the determining section determines that no residual water exists on the object 2 and the program proceeds from the end 112 in step 102 through steps 106 and 107 to step 108. The reference time T101a varies depending on the object 2 such as tweezers, scissors, forceps, endoscope, catheter, tray, hairdressing equipment, knives, cutting board and vaccine.

Figure 7:
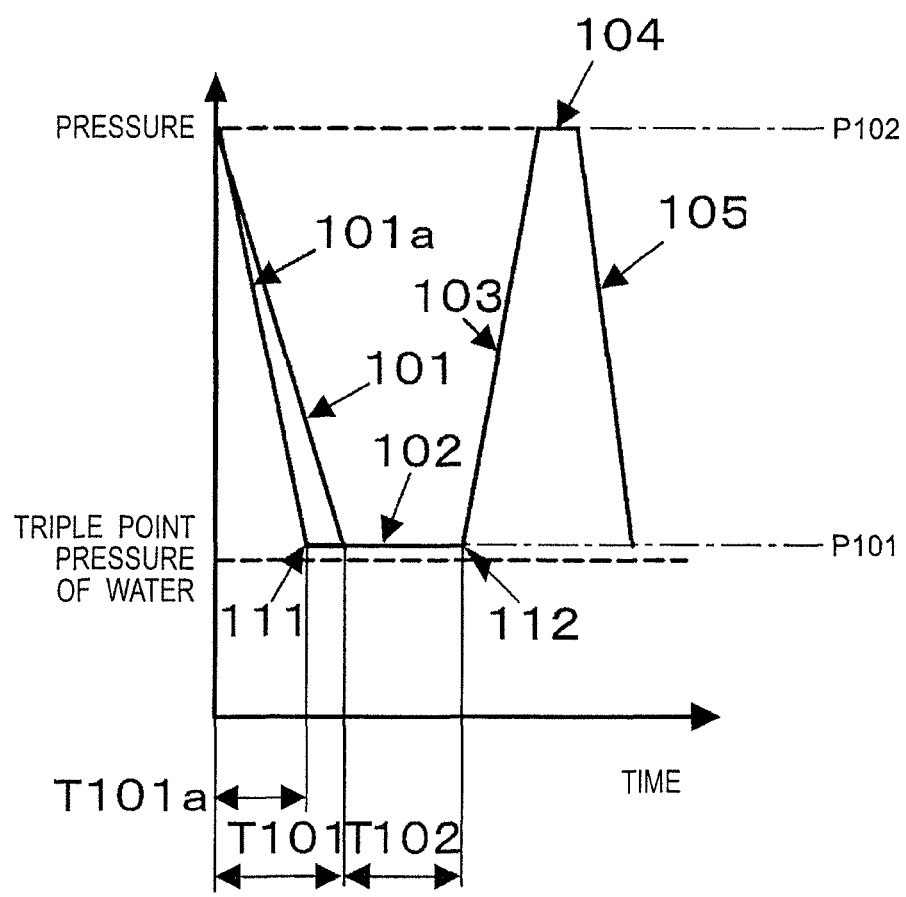
FIG. 7 is partial enlarged view of the graph in FIG. 5 showing an embodiment in which the residual water is detected.

FIG. 7 is a partial enlarged view of the graph in FIG. 5 showing an embodiment in which the residual water is detected by the determining section 25. In the series of processes shown in FIG. 7, if it is determined that the actual time T101 for actually decreasing the pressure to the first pressure P101 is greater than the reference time T101a, the determining section 25 determines that the residual water exists on the object 2 and the program proceeds from the end 112 in step 102 through steps 103 and 104 to step 105.

Figure 8:
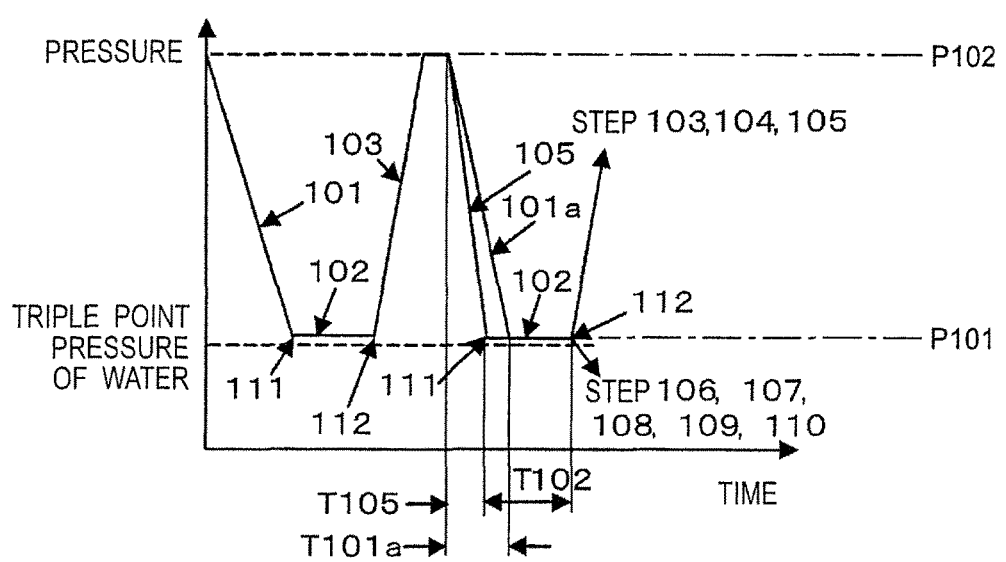
FIG. 8 is a graph showing the subsequent step of that shown in FIG. 7 in which the existence of residual water is determined.

If it is determined that the actual time T105 for completing step 105 is greater than the reference time T101a in the memory 27, it is determined that there exists the residual water and then the program proceeds from the end 112 of step 102 through steps 103 and 104 to step 105 to repeat the drying process as shown in FIG. 7. If, on the other hand, it is determined that T105 is equal to or less than T101a and then no residual water exists on the object 2, the program proceeds from the end 112 of step 102 through steps 106, 107, 108 and 109 to step 110 to terminate the sterilization step, as shown in FIG. 8.

If only a considerably small time or substantially no time is spent for step 104, the pressure in the container 11 at the beginning of step 105 may differ from the atmospheric pressure. In this instance, the actual time T105 in step 105 can vary. Therefore, at the beginning of step 105, a difference between the pressure in the container 11 measured by the pressure measuring unit 14 and the atmospheric pressure is calculated by the time calculating unit 28, which may be used for correcting the actual time T105 required for completing step 105 (see step #18 of FIG. 3C).

Alternatively, the number of repetition of the drying process may be limited. In this case, an error massage may be indicated on the display (not shown) of the sterilizer 1 and, if the drying process is repeated more than the predetermined number, the operation of the sterilizer 1 is terminated (see steps #20 and #21 of FIG. 3C). According to this arrangement, although the drying process is repeated as long as the residual water exists on the object 2, the pressure in the container 11 will never decrease less than the triple point pressure of water, which prevents the residual water on the object 2 from freezing. Also, the sterilant injection begins only after the residual water is removed. Therefore, no problem occurs which would otherwise be caused by the freezing of the residual water.

Figure 9:
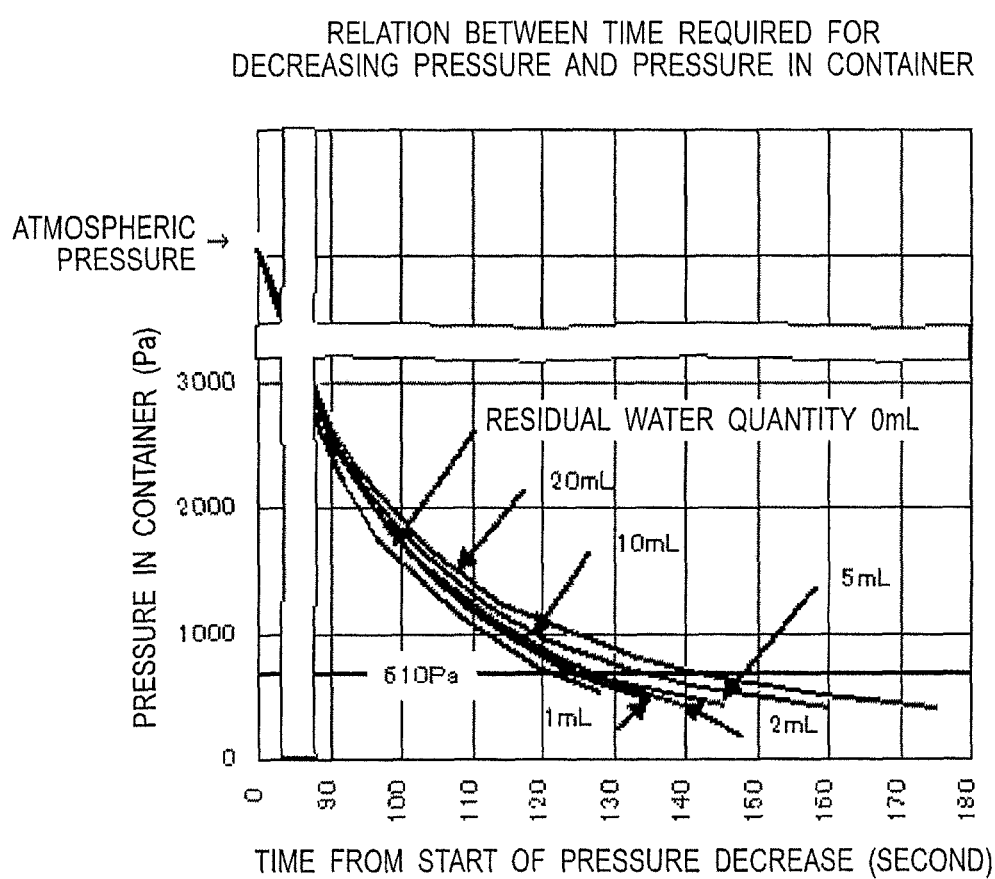
FIG. 9 is a graph showing a relationship between the pressure in the container and the time elapsed in the pressure reduction process obtained by an experiment in which an object, for example, a stainless tray was sterilized, according to the sterilization process described as the first embodiment of the invention.

FIG. 9 is a graph showing a relationship between the pressure in the container and the time elapsed in the pressure reduction process obtained by an experiment in which an object, for example, a stainless tray was sterilized according to the sterilization process described as the first embodiment of the invention. As shown in the drawing, the period of time T101 required for the pressure to reach the triple point pressure of water (610 Pa) from the beginning the pressure decreasing operation increases in proportion to the quantity of the residual water on the tray.

Figure 10:
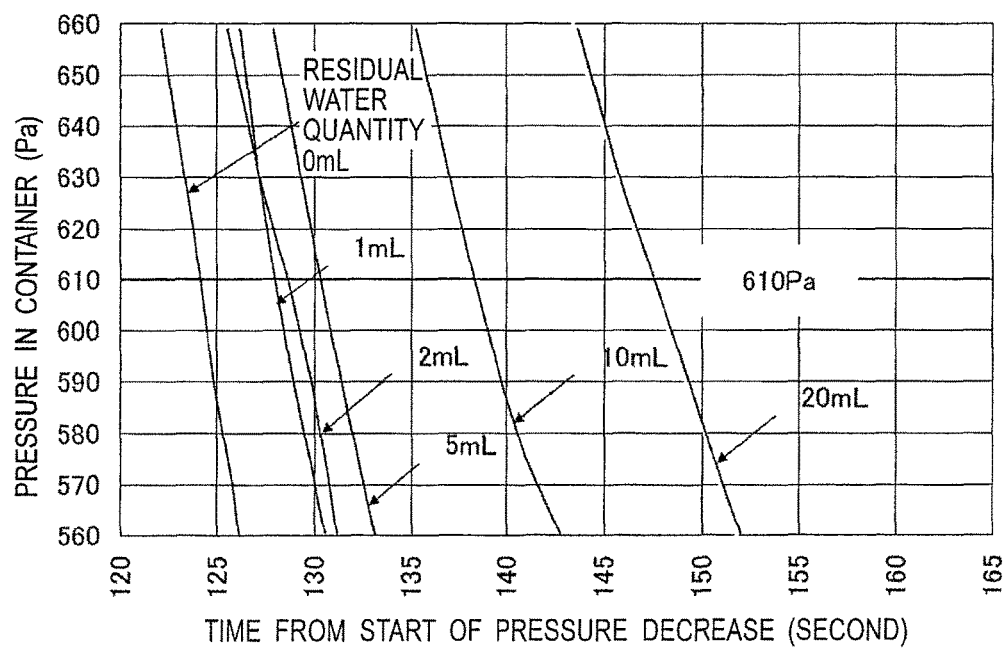
FIG. 10 is an enlarged view of the graph of FIG. 9 in which the pressure range in the vicinity of the triple point pressure of water is enlarged.

FIG. 10 is an enlarged graph showing a relationship between the pressure in the container and the time elapsed during which the pressure decreased near and to the triple point pressure of water 610 Pa in the experiment shown in FIG. 9. As shown in the drawing, there is a considerable difference between times T101 required for the pressure in the container to decrease to 610 Pa when no residual water existed and one milliliter or more of residual water existed. This means that a certain quantity of residual water in a range from zero to one milliliter may be employed as a threshold for determining the reference time T101a which is used in determining the existence of residual water in the container.

Figure 11:
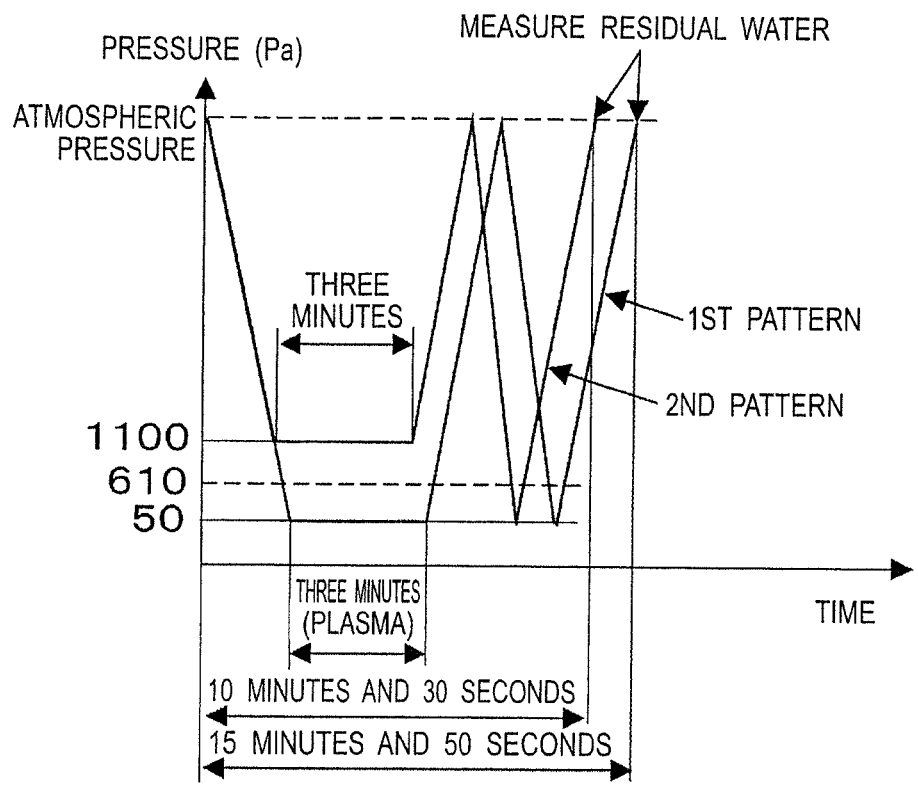
FIG. 11 is a graph showing an experimentally obtained quantity of the residual water depending on a pressure pattern in which the sterilization method according to the first embodiment is applied to the object to be sterilized, the object being an elongate hollow tube.

An experiment was made to examine an influence of pressure variation patterns to the quantity of residual water for an object made of an elongate hollow tube in the application of the sterilization process according to the first embodiment of the invention. The result is shown in FIG. 11. Two pressure patterns with a single heating process were used. Used as the object was a fluororesin PTFE tube having an outer diameter of 2.0 millimeters, an inner diameter of 1.0 millimeters, and a length of 3,700 millimeters. One end of the tube was closed, and the tube was filled with about 2.9 milliliter water. The water filled tube was placed in the container 11. The water in the tube was observed through a window provided on the container 11.

As shown in FIG. 11, the first pressure pattern is that described in Patent Document 1 in which the pressure in the container 11 was decreased continuously to 50 Pa which is lower than the triple point pressure of water (610 Pa) in the first pressure decreasing process and the decreased pressure 50 Pa was maintained for three minutes. Then, the pressure was increased to the atmospheric pressure in the drying step. Immediately after the drying process, the pressure was decreased again to 50 Pa and then increased up to the atmospheric pressure in which a quantity of the residual water was measured.

According to the first pressure pattern, the water in the tube began to evaporate due to the decompression boiling after starting the pressure decrease from the atmospheric pressure. Then, when the pressure reached about 300 Pa and 200 Pa below the triple point pressure of water (610 Pa), water began to freeze into ice at the opening of the tube, which prevented the water from moving out of the tube. To melt the ice, plasma energy was supplied into the container for three minutes under the reduced pressure of 50 Pa, but the ice was not removed completely and the water still remained in the tube.

The reason behind the ice remained in the tube is that, although a great amount of plasma is generated between the container (external bod) 11 and the internal box 12, a part of the generated plasma can passes through the perforations of the internal box 12 into the interior of the internal box 12 in which it diffuses throughout the interior of the internal box 12, so that only a significantly small amount of plasma can reach the object which is insufficient to melt the ice completely.

The ice at the opening of the tube was melted by maintaining the pressure in the container at 50 Pa for three minutes and then introducing the atmospheric pressure into the container. This is because the heat of the heated container 11 was transferred through the incoming air to the tube and then to the residual water to melt the ice. In the process of pressure decrease to 50 Pa, a part of the residual water in the tube is removed out of the tube due to the decompression boiling; however, the water was still observed in the tube at 50 Pa. Immediately after the pressure decreased to 50 Pa, the atmospheric pressure was introduced in the container 1 and then the tube was taken out of the container in which an amount of water remaining in the tube was measured, which showed that 0.6 milliliters of water existed.

The second pressure pattern is that described in the first embodiment of the invention, in which the pressure in the container 11 was decreased continuously to 1,100 Pa higher than the triple point pressure of water (610 Pa), the pressure 1,100 Pa was maintained for three minutes, the atmospheric pressure was introduced in the container, the pressure in the container is reduced again to 50 Pa, the atmospheric pressure was introduced in the container, and then an amount of residual water was measured.

In this pressure pattern, the water in the tube is evaporated after the pressure began to decrease from the atmospheric pressure due to the decompression boiling. The evaporation by the decompression boiling was maintained during which the pressure was maintained at 1,100 Pa less than the triple point pressure of water (610 Pa). This is because the heat of the tube was transferred for three minutes to the water cooled through the decompression boiling to maintain the boiling of the water. Although the water was observed in the tube after the elapse of three minutes in which the pressure in the container was maintained at 1,100 Pa, no water was frozen because the pressure in the container was maintained higher than the triple point pressure of water (610 Pa).

The pressure in the container was maintained at 1,100 Pa for three minutes and then increased to the atmospheric pressure, during which heat of the heated container 11 was transferred through the atmospheric air inflowing into the container 11, increasing the temperature of the tube and the residual water thereon. Then, in the process of decreasing the pressure in the container 11 to 50 Pa, the residual water in the tube was partly evaporated from the tube due to the decompression boiling. When the pressure reached 50 Pa, there was a little residual water observed in the tube. Then, the pressure was increased to the atmospheric pressure, and the tube was taken out of the container 11 in which an amount of water remaining in the tube was measured, which showed that 0.2 milliliters of water existed.

As such, the second method or the second pressure pattern according to the first embodiment of the present invention generated less residual water than the first method or the first pressure pattern according to the process described in Patent Document 1. The possible cause is that in the first method the water frozen into ice at the opening of the tube to prevent the water in the tube from being evaporated effectively while in the second method the generation of the ice was effectively prevented and the water evaporation was accelerated.

Therefore, in terms of evaporation of the residual water on the tube and its drying, the second method may be suitable than the first method because the freezing of the residual water can be prevented throughout the operation. Also, a period of time required from the beginning to the end of the operation of the first method is 15 minutes and 50 seconds which is greater than that of the second method (i.e., 10 minutes and 30 seconds), and therefore the second method is more preferably in terms of execution time and energy consumption.

Figure 12:
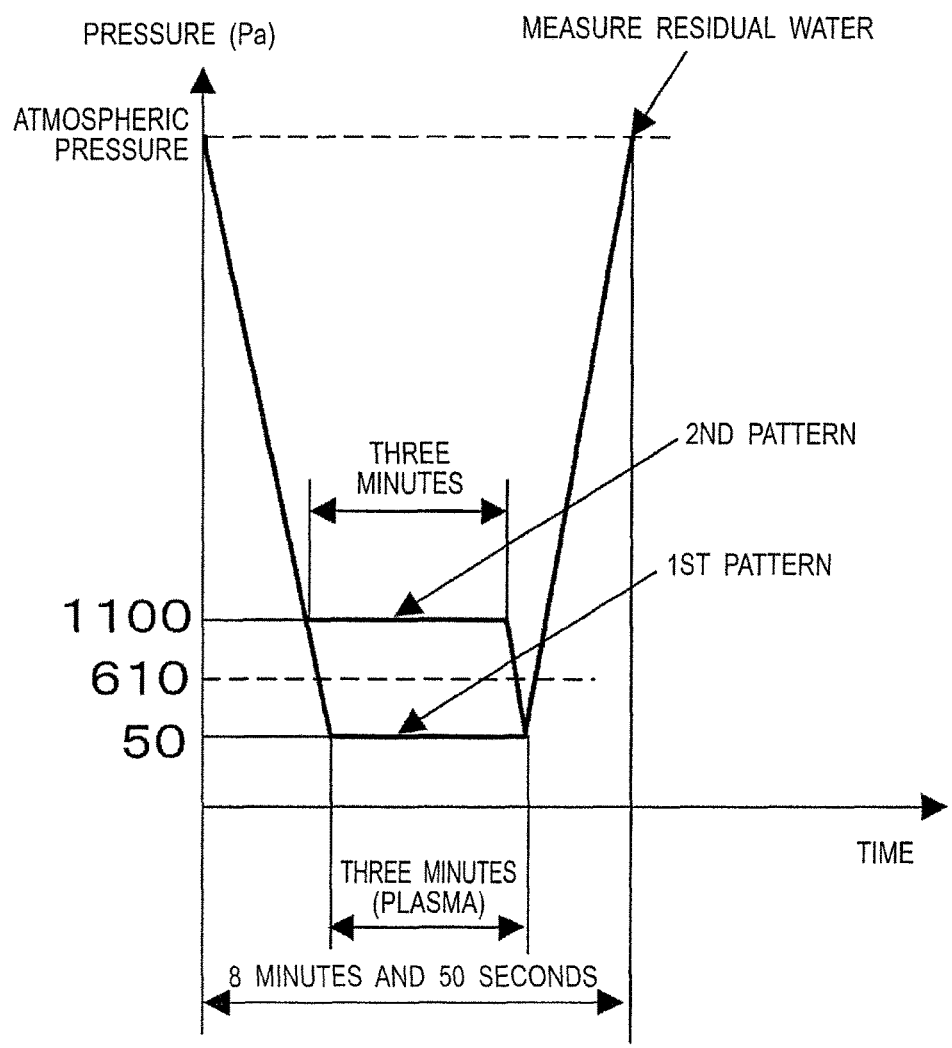
FIG. 12 is a graph showing an experimentally obtained quantity of the residual water depending on a pressure pattern in which the sterilization method according to the first embodiment is applied without a repetition of heating steps to an object to be sterilized, the object being an elongate hollow tube.

An experiment was made for determining a relation between the pressure pattern and the quantity of residual water for the object made of an elongate hollow tube, in which the heating process described in the first embodiment was not repeated. The result of the experiment is indicated in FIG. 12. In the experiment, two pressure patterns with a single heating process were performed. The object 2 was a PTFE (fluororesin) tube having an outer diameter of 2.0 millimeters, all inner diameter of 1.0 millimeters, and a length of 2,000 millimeters. One end of the tube was closed, and the tube was filled with about 1.6 milliliter water. The water filled tube was placed in the container 11. The water in the tube was observed through a window provided on the container 11.

In the first pressure pattern, as described in Patent Document 1, the pressure in the container 11 was decreased to 50 Pa lower than the triple point pressure of water (610 Pa). The pressure (50 Pa) was maintained for three minutes. Then the pressure was increased to the atmospheric pressure. In this process, the water began to evaporate immediately after the pressure decrease from the atmospheric pressure due to the decompression boiling. Then, the water began to freeze at the opening of the tube when the pressure decreased to about 300 to 200 Pa less than the triple point pressure of water (610 Pa), which prevented water from being evaporated from the tube. While the pressure of 50 Pa was maintained for three minutes, plasma was generated to supply heat energy for melting the frozen ice; however, the frozen ice was maintained at the opening of the tube and thereby the residual water was retained within the tube. The ice was melted in the process for increasing the pressure in the container in order to measure the residual water. The tube was taken out of the container and then the residual water was measured, which showed that 0.4 milliliters of residual water existed on the tube.

In the second pressure pattern which is the first embodiment of the present invention, the pressure in the container 11 was decreased to 1,100 Pa higher than the triple point pressure of water (610 Pa) in the first pressure decreasing process and the pressure (1,100 Pa) was maintained for three minutes. The pressure was decreased again to 50 Pa and then increased to the atmospheric pressure. According to this pattern, after the beginning of the pressure decrease from the atmospheric pressure, the water in the tube began to evaporate due to the decompression boiling. The evaporation of the water continued while the pressure, is maintained at 1,100 Pa greater than the triple point pressure of water (610 Pa) because the water cooled due to the decompression boiling was heated for three minutes by the tube and thereby the decompression boiling was maintained due to the temperature increase of the water. The pressure of 1,100 Pa was maintained for three minutes and then decreased to 50 Pa. Immediately thereafter, the pressure was increased to the atmospheric pressure, and the tube was taken out from the container 11. Then, the measurement was made to determine the quantity of water remaining on the tube; however, no residual water was detected.

The first method similar to that described in Patent Document 1 generated more residual water than that in the second method according to the first embodiment of the present invention. This is attributed to the fact that the ice blocks the opening of the tube to prevent the residual water from being vaporized effectively. Therefore, the second method capable of preventing the residual water from freezing throughout the operation is more preferably for vaporing the residual water and drying the tube. The first and second methods took substantially the same time, i.e., 8 minutes and 50 seconds for their operations.

Figure 13:
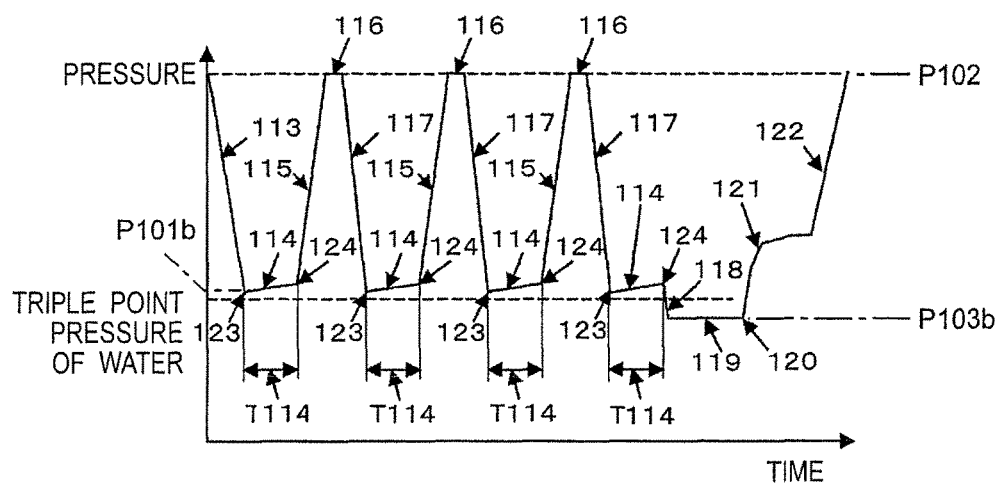
FIG. 13 is a graph showing a relationship between period of time and pressure in the container during the sterilization process according to the second embodiment of the invention.

Next, discussions will be made to a second embodiment of the invention with reference to a graph shown in FIG. 13 which illustrates a process for sterilizing an object with some residual water adhered thereon. FIG. 13 is a graph showing a relationship between period of time and pressure in the container during the sterilization process according to the second embodiment of the invention. Typically, according to the sterilization process in which the object is dried by using a decompression boiling, the interior of the container 11 is decompressed by means of an exhausting pump 20 and thereby the residual water on the object 2 is evaporated and then exhausted. By the evaporation of the water, the residual water loses its temperature; namely, it is cooled. This step is hereinafter referred to as "step 113".

According to the embodiment, in the pressure decreasing process in step 113 of the embodiment, the pressure in the container is decreased to the first pressure P101$b$ which is equal to or higher than the triple point pressure at which water freezes (610 Pa). The first pressure P101$b$ is preferably in a range between 610 Pa and 2,000 Pa, most preferably in a range between 670 Pa and 1,000 Pa. After the pressure is decreased to the first pressure. P101$b$, the solenoid valve 21 is closed. Then, the program proceeds to step 114 in which the pressure in the container 11 is increased from the first pressure P101$b$ through the evaporation of the residual water. As described below, it is determined at the end 124 of step 114 that the rate of pressure increase Rp114 from the first pressure P101$b$ is higher than the reference rate of pressure increase Rp114$a$, the program proceeds to step 115. The period of time T114 in step 114 is used to determining the rate of pressure increase Rp114.

In step 115, the solenoid valve 18 is opened to increase the pressure in the container 11 to the second pressure P102$b$ which is equal to or close to the atmospheric pressure, causing the object 2 to be exposed to the heated atmospheric air, which results in the increase in temperature of the object 2 and the residual water thereon. In step 116, the second pressure P102$b$ is maintained. During the entire period of time of step 116, heat is transferred from the atmospheric air to the object 2 and the residual water thereon. The period of time can be determined depending on the types of the objects 2.

The object 2 and the residual water thereon are heated during steps 115 and 116 so that they have at step 117 higher temperatures than those at the end 124 of step 114, which causes the residual water to evaporate through the decompression boiling. The drying process as described above is repeated through steps 115, 116, 117 and 114 in this order, thereby accelerating the drying of the residual water. When no residual water is detected at the end 124 of step 114, the method goes to step 119 through step 118. In step 119, the pressure in the container 11 is decreased to the third pressure P103b which is lower than or approximately equal to the first pressure P101b.

The third pressure P103b, which is suitable for injecting the sterilant into the container 31 and for generating plasma, is preferably in a range between 30 Pa and 200 Pa. The third pressure P103b is lower than the triple point pressure at which water freezes (610 Pa). The drying process removes the residual water which might otherwise generate ice on the object 2.

After the pressure in the container 11 is decreased to the third pressure P103b, for the purpose of heating the container 11 (the external box), the internal box 12, and the object 2, a high-frequency wave 13 from the high-frequency generator 13 may be applied between the container 11 and the internal box 12 to generate the plasma. At the end 120 of step 119, a predetermined quantity of the sterilant is injected via the solenoid valve 9 into the container 11 in the form of steam or vapor. In step 121, the injected sterilant passes the perforations of the internal box and subsequently adheres to the object 2. A certain time necessary for the effective sterilization is allocated to step 121. After the completion of step 121, the pressure in the container 11 is increased to the second pressure P102b, which terminates the first sterilization step. Preferably, step 109 is repeated to enhance the sterilization effect.

Figure 14:
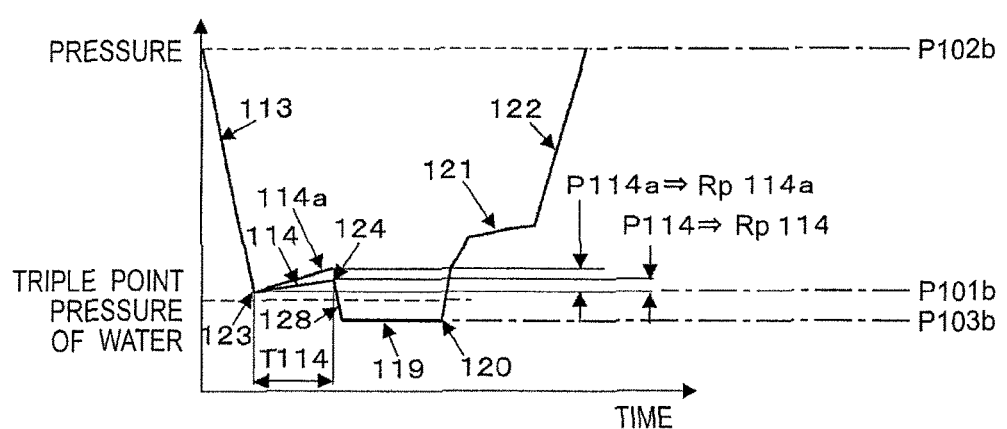
FIG. 14 is an enlarged view of the graph of FIG. 13 in which no residual water is detected.

FIG. 14 is an enlarged view of the graph of FIG. 13 for the operation in which no residual water is detected. As shown in this drawing, when no residual water is detected on the object 2 by the determining section 25 at the end 124 of step 114, the rate of pressure increase Rp114 is calculated by the pressure increasing rate determining unit 30, using a difference between the pressure P123 at the start 123 and the pressure at the end 124 of step 114 which are measured by the pressure measuring unit 14, and the period of time T114 spend in step 114.

The memory 31 stores the reference rate of pressure increase Rp114a in which no residual water is detected. The rate of pressure increase in the container 11 correlates with the quantity of the residual water on the object 2 so that a vapor pressure as well as the rate of pressure increases as the quantity of the residual water. The measured rate of pressure increase Rp114 is compared with the reference rate of pressure increase Rp114a and it is determined that Rp114 is equal to or less than Rp114a, it is determined that no residual water exists on the object 2 by the determining section 25. Then, the program proceeds from the end 124 of step 114 through steps 118, 119 and 121 to step 122 in this order. The reference rate of pressure increase Rp114a varies depending on the types of the objects 2 such as tweezers, scissors, forceps, endoscope, catheter, tray, hairdressing equipment, knives, cutting board and vaccine.

Figure 15:
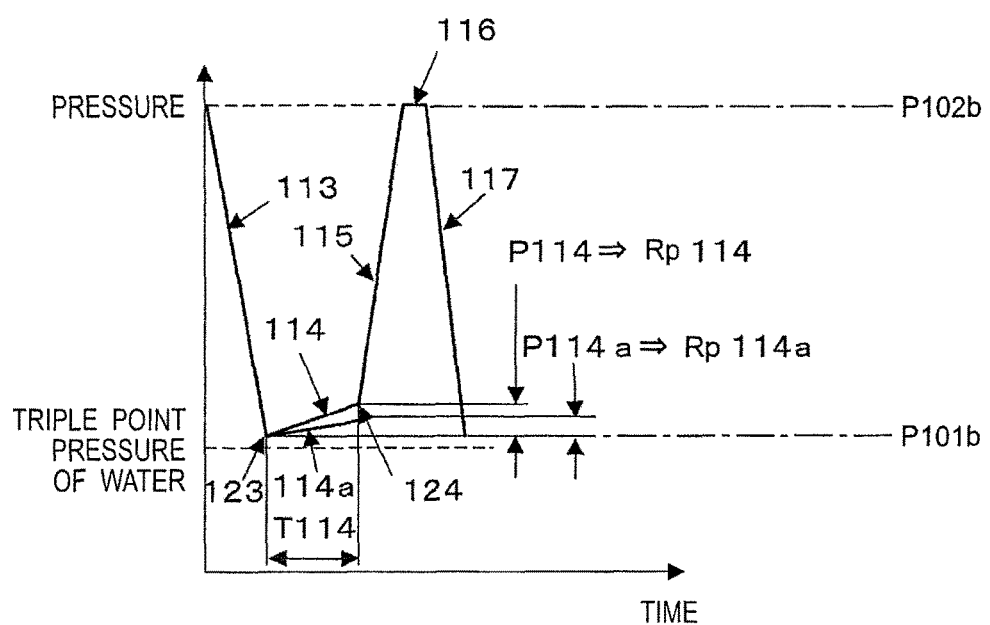
FIG. 15 is an enlarged view of the graph of FIG. 13 in which the residual water is detected.
Figure 16:
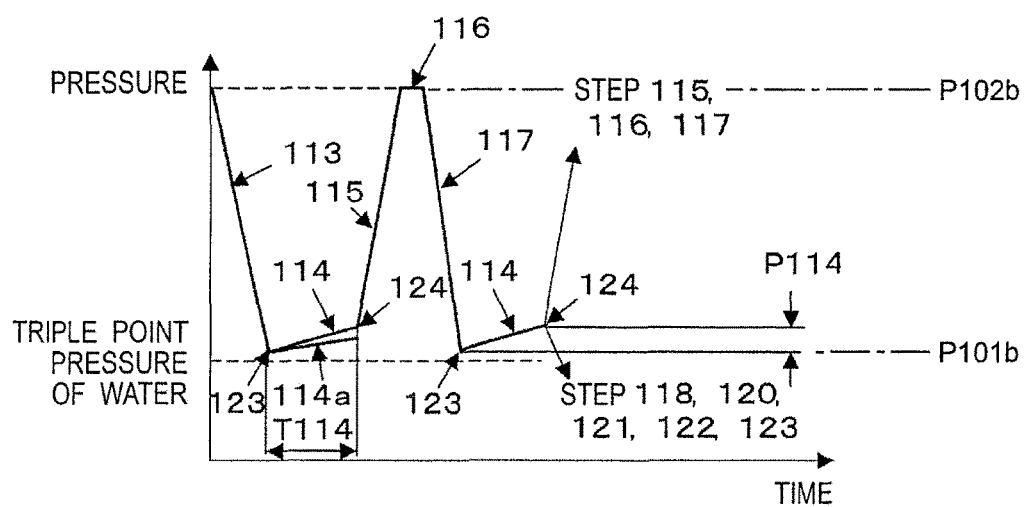
FIG. 16 is a graph showing a process subsequent to that shown in FIG. 15 in which it is determined whether the residual water exists on the object.

FIG. 15 is an enlarged view showing a part of the graph FIG. 13 which illustrates an operation performed when it is determined that the residual water exists on the object. FIG. 16 is a graph showing a process subsequent to that shown in FIG. 15 in which it is determined whether the residual water exists on the object. If it is determined by the comparator 33 that the actual rate of pressure increase Rp114 is greater than the reference rate of pressure increase Rp114a and, as a result, it is determined by the determining section 25 that the residual water exists on the object, as shown in FIG. 5 the program proceeds from the end 124 of step 114 to the drying process performed in steps 115, 116, 117 and 114.

If on the other hand it is determined by the comparator 33 that the actual rate of pressure increase Rp114 is equal to or less than the reference rate of pressure increase Rp114a and, as a result, it is determined that no residual water exists on the object, the program proceeds from the end 124 of step 114 through steps 118, 119 and 121 to step 122 to terminate the sterilization step.

Alternatively, the number of repetition of the drying process may be limited. In this case, an error message may be indicated on the display (not shown) of the sterilizer 1 if the drying process is repeated more than a predetermined number and also the sterilizer 1 is deactivated in steps #51 and #52 of FIG. 4C. According to this arrangement, if it is determined that the residual water exists on the object 2, the drying process is repeated. During this operation, the pressure in the container 11 is maintained less than the triple point pressure of water, which prevents the residual water on the object 2 from freezing. Also, the sterilant is injected only after the removal of the residual water and therefore no freezing occurs on the object.

In connection with the sterilization method according to the second embodiment of the invention, an experiment was made to determine the rate of pressure increase in a process in which the pressure in the container 11 is decreased to a certain value greater than the triple point pressure of water, for respective quantities of residual water in the container. The result is shown in FIG. 17 which illustrates a relationship between the pressure in the container 11 and time elapsed after the pressure in the container 11 reached 1,000 Pa at which the solenoid valve 21 connected to the air displacement pump 20 was opened.

Specifically, the experiment was made by disposing a plastic tray or bowl in the container 11, placing a certain amount of water on the tray, opening a solenoid valve 21 to decrease the pressure in the container to 1,000 Pa (which is higher than the triple point pressure of water 610 Pa), and then closing the solenoid valve 21. A relationship was experimentally determined between a period of time elapsed after the pressure in the container 11 reached 1,000 Pa and the pressure in the container 11. The experiment was performed for five different quantities of residual water ranging between 0 and 50 milliliter.

Figure 17:
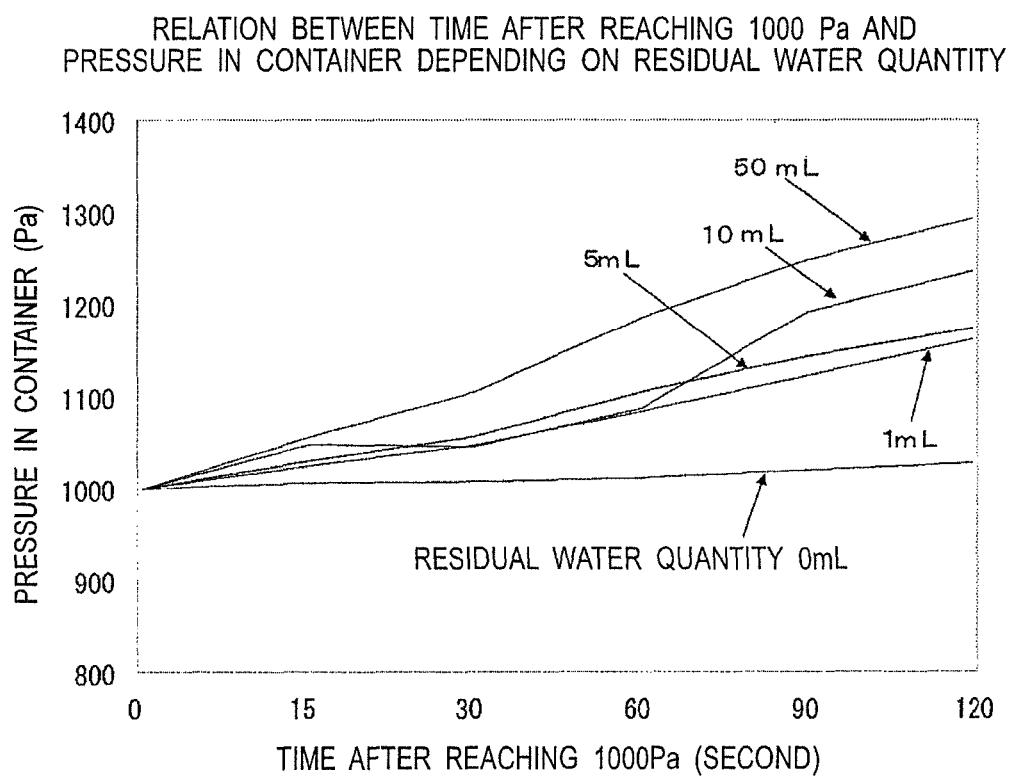
FIG. 17 is a graph showing experimentally obtained rates of pressure increase after the pressure was decreased to a pressure which is equal to or higher than the triple point pressure of water, under varying quantities of the residual water in the container as parameters.

As can be seen from FIG. 17, the rate of pressure increase in which no residual water existed is evidently different from that in which the more than one milliliter of residual water existed. This means that a certain quantity of residual water in a range from zero to one milliliter may be employed as a threshold for determining the existence of residual water.

Figure 18:
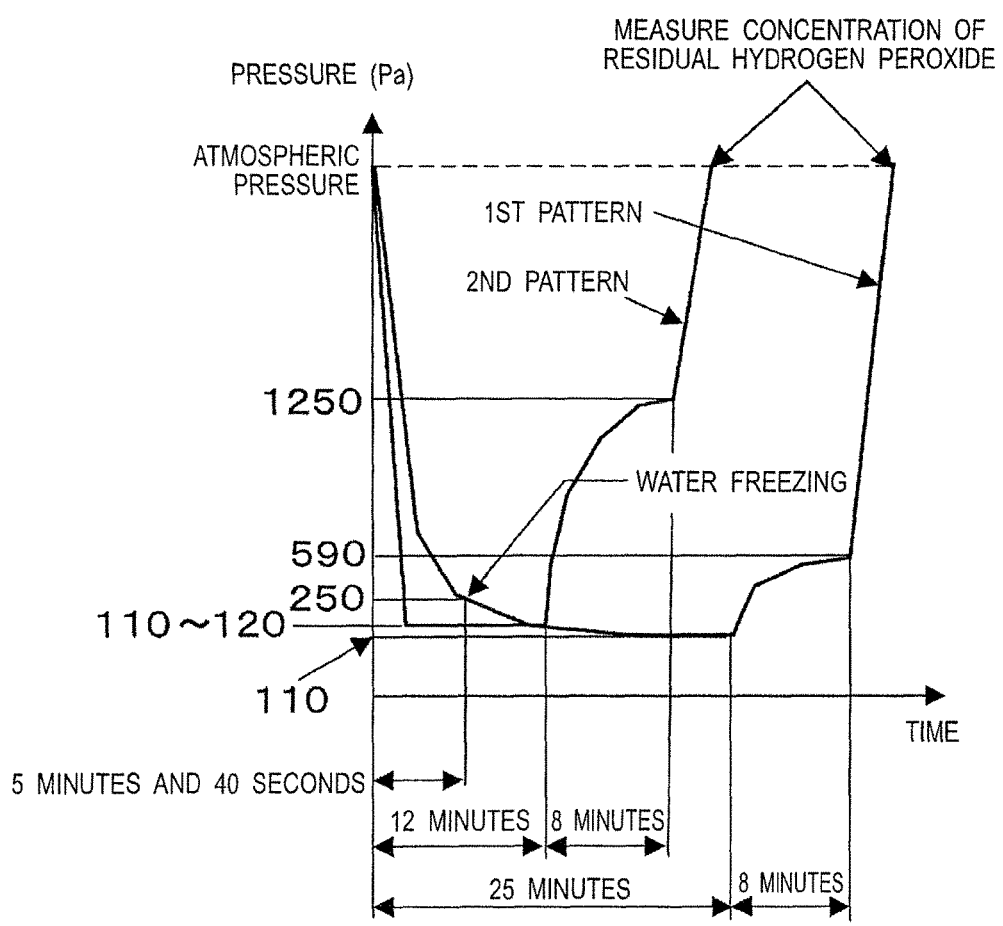
FIG. 18 is a graph showing pressure patterns for an experiment for detecting the residual water and the freezing thereof, and for determining a quantity of the residual sterilant on the object to be sterilized.

An experiment was made for determining the existence of residual water on the object 2 and its freezing and for determining a quantity of the residual sterilant on the object 2 in the container 11. FIG. 18 is a graph showing a variation of the pressure together with a point of freezing and points of measuring the concentration of the residual hydrogen peroxide. In this experiment, the quantities of the residual sterilant on the object 2 were measured in the first and second patterns and the measurements were compared. In the first pattern, the sterilant was injected in the container in which the frozen water existed on the object. In the second pattern, the sterilant was injected in the container in which no water existed on the object.

In the first pattern, the sterilant was injected into the container in which the residual water frozen. Specifically, the first pattern included disposing a stainless tray with 50 gram water received thereon in the container 11, and decreasing the pressure in the container 11. In the pressure decreasing process, the water frozen into ice when the pressure decreased to 250 Pa (less than the triple point pressure of water 610 Pa). The pressure decreasing continued for 25 minutes at which the pressure in the container reached 110 Pa. In this condition, 2.2 milliliter sterilant containing 60 percent hydrogen peroxide was injected into the container 11. After eight minutes elapsed, the pressure in the container increased due to the evaporation of the hydrogen peroxide to 590 Pa. Then, the pressure was increased to the atmospheric pressure.

Then, the tray was taken out of the container 11 and was washed after melting the ice on the tray into a solution of hydrogen peroxide. The concentration and the weight of the hydrogen peroxide were measured to determine the quantity of the residual hydrogen peroxide on the tray. The measured quantity of residual hydrogen peroxide per unit area on the tray was 1.2 mg/cm$^2$.

In the second pattern according to the embodiment of the present invention, the sterilant was injected in the container in which no the residual water or ice existed. Specifically, a dried stainless-steel tray was placed in the container 11 and the pressure in the container was decreased. Then, the pressure in the container 11 was maintained in a range between 110 Pa to 120 Pa. After 25 minutes elapsed from the start of the pressure decreasing process, 2.2 milliliter sterilant containing 60 percent hydrogen peroxide was injected into the container 11. After eight minutes elapsed, the pressure in the container increased to 1,250 Pa due to the evaporation of the hydrogen peroxide. Then, the pressure in the container was increased to the atmospheric pressure.

The tray was taken out of the container 11 and an appropriate amount of water was put on the tray to wash tray and to generate a solution of hydrogen peroxide. Using the weight of the solution and the concentration of hydrogen peroxide in the solution, the quantity of the residual hydrogen peroxide on the tray was measured. The measured quantity of hydrogen peroxide per unit area was 0.0053 mg/cm$^2$.

Experiments were made using the first to third patterns. Although not illustrated, in the third pattern the sterilant was injected in the container in which no residual water or ice exists as was done in the second pattern.

Specifically, water of 10 g was placed on a stainless-steel tray which was disposed in the container 11. The pressure in the container 11 was decreased to 700 Pa to 800 Pa which was higher than the triple point pressure of water 610 Pa. Then, (a) the decreased pressure was maintained for a minute, (b) the pressure was increased to the atmospheric pressure which was maintained for five minutes, and (c) the pressure was decreased again. These steps (a) to (c) were repeated eight times. After confirmed the fact that no water existed on the tray, the pressure was decreased to 60 Pa which was maintained for 12 minutes. 2.2 milliliter sterilant containing 60 percent hydrogen peroxide was injected into the container 11. After eight minutes elapsed, the pressure in the container increased to 2,300 Pa due to the evaporation of the hydrogen peroxide. Then, the pressure in the container 11 was increased to the atmospheric pressure.

The tray was taken out of the container 11 and an appropriate amount of water was placed on the tray which tray was then washed to generate a solution of hydrogen peroxide. Using the weight of the solution and the concentration of hydrogen peroxide in the solution, the quantity of the residual hydrogen peroxide on the tray was measured. The measured quantity of hydrogen peroxide per unit area was 0.0019 mg/cm$^2$.

The following table 1 shows the results of the experiments using first to third patterns.

TABLE 1

|  | First Pattern frozen sample (comparative example) | Second Pattern contrast | Third Pattern sample dried under decreased pressure (working example) |
| --- | --- | --- | --- |
| distilled water | 50 g | — | 10 g |
| pressure increase/ decrease | decreasing to 100 Pa | decreasing to 100 Pa | (decreasing to 800 Pa ⇔ atmospheric pressure• providing heat) × 8 + decreasing to 80 Pa |
| state during pressure decreasing | moisture frozen | no change | no change |
| sterilant injection | 2.2 ml | 2.2 ml | 2.4 ml |
| state after injection | ice wet | no change | no change |
| vapor pressure after 8 minutes | 590 Pa | 1,240 Pa | 2,300 Pa |
| tray after treatment | ice, wet in its entirety•cold | dry, not cold | dry, not cold |
| residual hydrogen peroxide | 1.2 mg/cm$^2$ | 0.0053 mg/cm$^2$ | 0.0019 mg/cm$^2$ |

The result shows that, when the sterilant is injected in the container under the existence of ice, the following problems occurs.

(1) The amount of sterilant remaining on the tray is 240 times as much as that measured under the existence of ice. This is considered to be attributed to the sterilant vapor which adheres to the low temperature tray and the ice thereon to cause condensation, which results in a considerable quantity of residual sterilant.

(2) The sterilant concentrates on the low temperature tray and the ice, which results in highly concentrated areas which may cause problems with the residual sterilant and little concentrated areas which may cause problems with defective sterilization.

(3) Little sterilant adheres to the surface portions of the object supporting ice generated thereon, which results in a defective sterilization of the object. Namely, the residual water on the object may be frozen to ice by the decompression, which results in problems due to the existence of the residual sterilant and also in defective sterilization of the object.

According to the sterilization method of the invention, no ice is generated on the object 2 and the pressure in the container is not decreased less than the triple point pressure of water before the object is completely dried, which overcomes the above described problems.

As such, the sterilization method according to the invention prevents the residual water from freezing into ice on the object or in the vicinity thereof in the sterilization process in which the container is decompressed and then the object is sterilized. That is that the condensation of the sterilant and the defective sterilization are overcome by the drying process which is conducted under the pressure more than the triple point pressure of water and by the sterilizing process which is conducted after confirming that the interior of the container is fully dried.

The sterilization method and the sterilizer according to the present invention are applicable to various types of sterilizers such as a gas plasma sterilizer, a sterilizer using hydrogen peroxide, a sterilizer using peracetic acid vapor, in which a method including a step of decreasing the pressure less than the triple point pressure of water. The object 2 may include various things such as cut vegetables, herbs, leaves of tobacco, plant seeds, eggs, rice, tea, or mushrooms. Further, they are applicable to various purposes such as keeping freshness, preventing flavor deterioration, drying foods, removing odor from shoes, and sterilizing the soil.

INDUSTRIAL APPLICABILITY

The present invention is effectively used in a method for sterilizing an object to be sterilized in a decompressed container using a sterilant and a sterilizer.

DESCRIPTION OF REFERENCE SYMBOLS 1 sterilizer
2 object to be sterilized
6 sterilant supply system
7 tank for the sterilant
8 sterilant injector
9 sterilant injection solenoid valve
10 sterilization system
11 container
12 internal box
13 high-frequency generator
14 pressure measuring unit
15 intake/exhaust piping system
16 intake piping system
17 air filter
18 introduction solenoid valve
19 exhaust piping system
20 air displacement pump
21 solenoid valve for evacuation
22 exhaust gas filter
23 controller
24 operator
25 determination section
26 time measurement unit
27 memory
28 time comparator
29 time calculating unit
30 pressure increasing rate determining unit
31 memory related to the rate of pressure increase
32 calculator for the rate of pressure increase
33 comparator for the rate of pressure increase
P101 pressure which is equal to or higher than the triple point pressure of water
P103 pressure which is equal to or lower than the triple point pressure of water
T101 actual time required for decreasing the pressure to the first pressure P101
T101a reference time for decreasing the pressure to the first pressure P101
Rp114 actual rate of pressure increase (percent)
Rp114 reference rate of pressure increase (percent)
T102 certain period of time
T105 period of time for completing step 105
T106 period of time for maintain the second pressure P102b

The invention claimed is:

1. A method for sterilizing an object in a container using a sterilant, the method comprising the steps of:
   (A1) decreasing a pressure in a container from a pressure at a beginning of pressure reduction to a first pressure which is equal to or more than the triple point pressure of water;
   (A2) maintaining the first pressure in the container;
   (A4) decreasing the pressure in the container to a third pressure which is substantially equal to or less than the first pressure,
   (A5) injecting the sterilant into the container; and
   (A6) determining whether residual water exists in the container based on an actual time in which the pressure in the container is decreased to the first pressure,
      wherein the step (A6) comprises correcting the actual time using a difference between an atmospheric pressure and the pressure at the beginning of pressure reduction; and comparing a reference time stored in a memory and the corrected actual time, and
      wherein, if the corrected actual time is equal to or less than the reference time, it is determined that no residual water exists.

2. The method according to claim 1, further comprising the steps of:
   (A3) increasing the pressure in the container to a second pressure which is equal to or close to an atmospheric pressure; and
   wherein the step (A3) is performed after the step (A2) and before the step (A4).

3. The method according to claim 2, wherein the steps (A3), (A1) and (A6) are performed in this order if it is determined in the step (A6) that the residual water exists, and wherein the steps (A4) and (A5) are performed in this order if it is determined in the step (A6) that the residual water does not exist.

4. The method according to claim 1, wherein the step (A5) comprises injecting the sterilant into the container at a certain pressure in the container which is equal to or less than the triple point pressure of water.

* * * * *